United States Patent
Pracheil et al.

(10) Patent No.: US 12,247,991 B2
(45) Date of Patent: Mar. 11, 2025

(54) REMOTE AUTONOMOUS ENVIRONMENTAL DNA SAMPLER AND ANALYZER

(71) Applicants: UT-Battelle, LLC, Oak Ridge, TN (US); Caroline Carter, Plano, TX (US)

(72) Inventors: Brenda M. Pracheil, Knoxville, TN (US); Phillip C. Chesser, Knoxville, TN (US); Natalie A. Griffiths, Knoxville, TN (US); Kristine Moody, Knoxville, TN (US); Brian K. Post, Knoxville, TN (US); Brennan T. Smith, Knoxville, TN (US); Peter Wang, Oak Ridge, TN (US); Caroline Carter, Plano, TX (US); Celeste Atkins, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 18/374,953

(22) Filed: Sep. 29, 2023

(65) Prior Publication Data
US 2024/0248105 A1 Jul. 25, 2024

Related U.S. Application Data

(60) Provisional application No. 63/440,506, filed on Jan. 23, 2023.

(51) Int. Cl.
*G01N 1/10* (2006.01)
*C12Q 1/6806* (2018.01)
(Continued)

(52) U.S. Cl.
CPC ....... *G01N 35/0099* (2013.01); *C12Q 1/6806* (2013.01); *C12Q 1/6869* (2013.01);
(Continued)

(58) Field of Classification Search
CPC ............... G01N 35/00871; G01N 1/10; G01N 35/0099; C12Q 1/6806
See application file for complete search history.

(56) References Cited

U.S. PATENT DOCUMENTS

2002/0049012 A1\* 4/2002 Kirkwood ............... F42B 19/12
440/67
2015/0224502 A1\* 8/2015 Pargett ............... G01N 33/1893
422/509
(Continued)

FOREIGN PATENT DOCUMENTS

WO 2022/040749 A1 3/2022

OTHER PUBLICATIONS

Niiler, E. 'Environmental DNA' Lets Scientists Probe Underwater Life [online] Feb. 21, 2020 [retrieved on Apr. 19, 2024] retrieved from https://www.wired.com/story/environmental-dna-lets-scientists-probe-underwater-life/ (Year: 2020).\*
(Continued)

*Primary Examiner* — Samuel C Woolwine
*Assistant Examiner* — Lisa Horth
(74) *Attorney, Agent, or Firm* — FOX ROTHSCHILD LLP

(57) ABSTRACT

Systems and methods for operating an aquatic robot. The methods comprise: autonomously propelling the aquatic robot through a body of water to a location where a water sample is to be obtained; and performing operations by the aquatic robot to autonomously collect the water sample, cause the water sample to flow through a filter that retains eDNA, lyses and releases the eDNA to a create a lysate, process the lysate to obtain a product for eDNA sequencing, generate eDNA sequencing data using the product, and communicate the eDNA sequencing data to a remote external device.

16 Claims, 17 Drawing Sheets

(51) Int. Cl.
*C12Q 1/6869* (2018.01)
*G01N 35/00* (2006.01)
*G01N 1/40* (2006.01)

(52) U.S. Cl.
CPC ......... *G01N 1/10* (2013.01); *G01N 35/00871* (2013.01); *G01N 2001/1031* (2013.01); *G01N 2001/4088* (2013.01)

(56) References Cited

U.S. PATENT DOCUMENTS

2015/0275291 A1  10/2015  Fehr
2022/0033872 A1*  2/2022  Magalhães ............... G01N 1/12
2022/0323963 A1*  10/2022  Ohiri ................. B01L 3/502715

OTHER PUBLICATIONS

Das, et al. Data-driven robotic sampling for marine ecosystem monitoring. The International Journal of Robotics Research 34(12):1435-1452 (2015). (Year: 2015).*

Yamahara et al., "In situ Autonomous Acquisition and Preservation of Marine Environmental DNA Using an Autonomous Underwater Vehicle", Jul. 16, 2019 (Jul. 16, 2019), Front Mar. Sci. Sec. Marine Molecular Biology and Ecology vol. 6—2019, https://doi.org/10.3389/fmars.2019.00373; entire document, especially abstract, p. 2 col 2 para 1-2, p. 5 col 1 para 1—col. 2 para 1.

Formel et al., "Subsurface automated samplers for eDNA (SASe) for biological monitoring and 1-20 research", Oct. 2021 (Oct. 2021), HardwareX 10 (2021) https://doi.org/10.1016/j.ohx.2021.e00239; entire document.

International Search Report and Written Opinion mailed on Feb. 7, 2024 in PCT/US23/34124.

Preston et al.: "Underwater Application of Quantitative PCR on an Ocean Mooring", Plos One. 2011;6(8).

Hansen et al.: "Remote, autonomous real-time monitoring of environmental DNA from commercial fish", Sci Rep-Uk. 2020;10(1).

Ahrberg et al.: "Polymerase chain reaction in microfluidic devices", Lab Chip. 2016; 16(20):3866-84.

Chung et al.: "Microfluidic chip for high efficiency DNA extraction", Lab Chip. 2004;4(2):141-7.

Geissler et al.: Centrifugal microfluidic lab-on-a-chip system with automated sample lysis, DNA amplification and microarray hybridization for identification of enterohemorrhagic *Escherichia coli* culture isolates:, Analyst. 2020;145(21):6831-45.

Pol et al.: "Microfluidic lab-on-a-chip platforms for environmental monitoring", Trac-Trend Anal Chem. 2017;95:62-8.

* cited by examiner

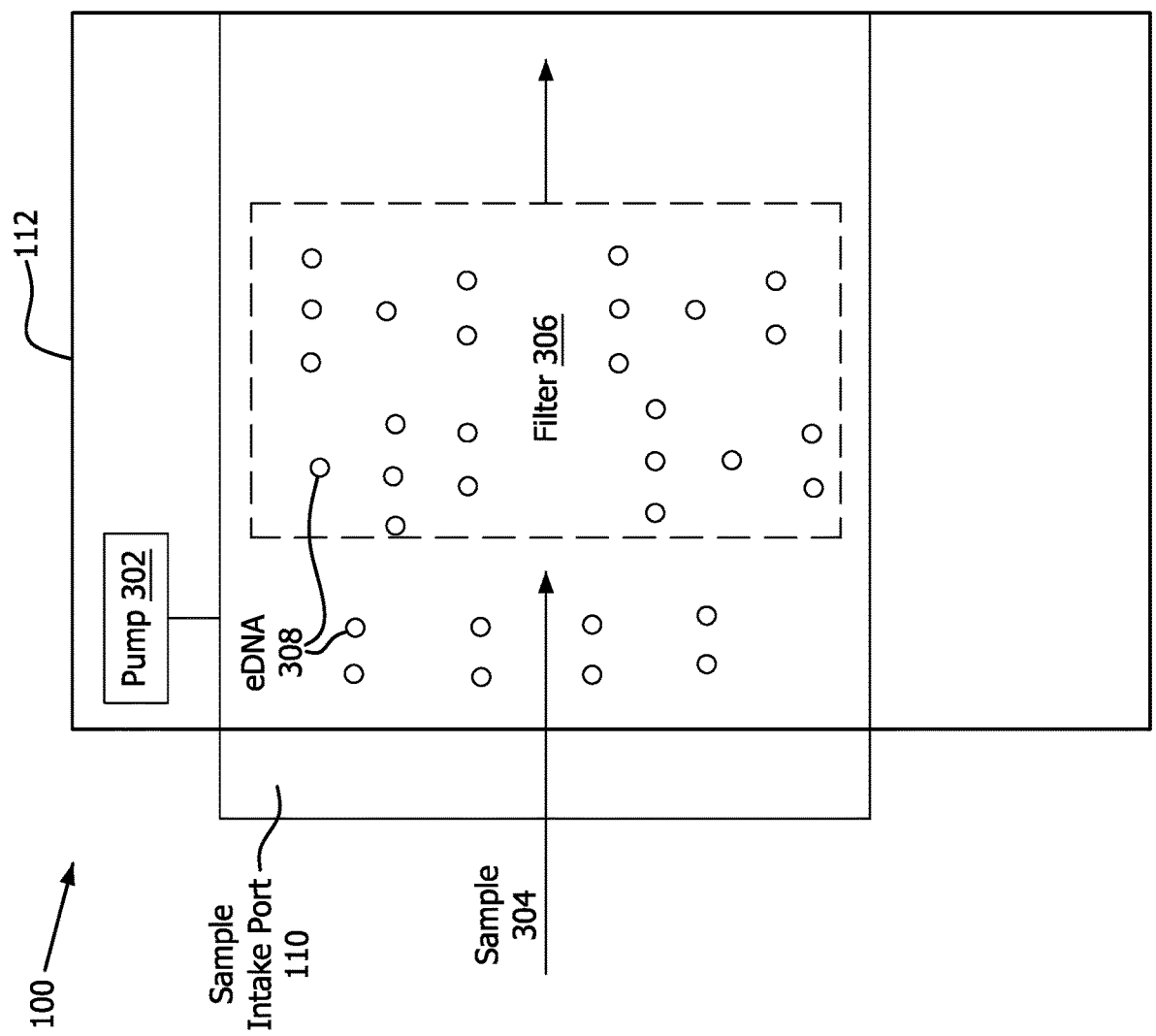

REMOTE AUTONOMOUS ENVIRONMENTAL DNA SAMPLER AND ANALYZER

CROSS-REFERENCE TO RELATED APPLICATIONS

The present application claims priority to and the benefit of U.S. Provisional Patent Application Ser. No. 63/440,506 which was filed on Jan. 23, 2023. The content of this Provisional Patent Application is incorporated herein by reference in its entirety.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in this invention.

FIELD OF THE INVENTION

The present document relates to electrical generators. More particularly, the present document concerns direct drive modular permanent magnet are generators.

BACKGROUND

Traditional biodiversity survey methods are time-consuming, costly and present health and safety risks for personnel, as well as introduce bias resulting in misrepresentation of the true biotic community. Interactions between humans and wildlife can lead to biodiversity declines and increased emergence of zoonotic diseases. In this way, conversations about biodiversity conservation and human health go hand-in-hand. It is, therefore, imperative that biodiversity assessments are accurate, timely and cost-effective.

SUMMARY

The present document concerns a method for operating an aquatic robot. The methods comprise: autonomously propelling the aquatic robot through a body of water to a location where a water sample is to be obtained; and performing operations by the aquatic robot to autonomously collect the water sample, cause the water sample to flow through a filter that retains eDNA, lyses the cells and releases the eDNA from the filter (unprocessed lysate), clean the unprocessed lysate to obtain a purified eDNA, constructs (PCR amplification, adapter annealing, and cleaning) next generation sequencing libraries, generates eDNA sequencing data using the product in near-real-time, and either communicates the eDNA sequencing data to a remote external device for bioinformatic analysis, or conducts bioinformatic analysis on-board.

The methods may also involve: autonomously propelling the aquatic robot through the body of water to another different location where another water sample will be obtained; and repeating the operations by the aquatic robot using another different water sample. The another different location may be selected randomly, from a plurality of user-defined locations, or selected based on machine learned information.

Additionally or alternatively, the filter is integrated with a manifold into a single assembly. The single assembly may comprise: a stationary part; a removable part removably coupled to the stationary part; an inlet channel extending around a circumference of the removable part and configured to cause a fluid to flow from an inlet port towards the filter that is disposed inside the removable part; and an outlet channel spaced apart from the inlet channel, extending around the circumference of the removable part, and configured to cause a filtered fluid to flow from the filter to an outlet port of the single assembly. Accordingly, the method can also comprise autonomously decoupling the removable part from the stationary part, replacing the filter with another filter, and re-coupling the removable part to the stationary part.

Additionally or alternatively, the lysate is processed using a micro- or milli-fluidics system. The fluidics system may comprise a 3D printed part. The method may also comprise: using a fluid channel of the micro- or milli-fluidics system to transport the lysate to at least one mixing channel having a spiral shape configured to facilitate mixing of the lysate with a cleaning solution; using a surface tension on the fluid and an internal pressure of the micro- or milli-fluidics system to control a flow of the fluid from a fluid holding area inside the micro- or milli-fluidics system to the at least one mixing channel; allowing the fluid to flow from the at least one mixing channel and through another filter configured to retain DNA; transporting a release agent within the micro- or milli-fluidics system to the another filter for releasing the eDNA therefrom; and/or transporting the released and purified eDNA out of the micro- or milli-fluidics system.

The present document concerns a system comprising a propulsion system and an aquatic robot. The aquatic robot is configured to (i) autonomously control the propulsion system to be propelled through a body of water and (ii) perform sequencing operations to autonomously collect a water sample at a location in the body of water to which the aquatic robot was propelled, cause the water sample to flow through a filter that retains eDNA, lyses the cells and releases the eDNA (unprocessed lysate), cleans the unprocessed lysate to obtain purified eDNA for next-generation library construction (PCR amplification, adapter annealing, and cleaning), generates eDNA sequencing data using the product, and communicates the eDNA sequencing data to a remote external device for bioinformatic analysis or results of the on-board bioinformatic analysis.

The aquatic robot may also be configured to: control the propulsion system to be autonomously propelled through the body of water to another different location where another water sample is to be obtained; and repeat the sequencing operations using the another water sample. The another different location may be selected randomly, from a plurality of user-defined locations, or based on machine learned information.

The filter may be integrated with a manifold into a single assembly. The single assembly may comprise: a stationary part; a removable part removably coupled to the stationary part; an inlet channel extending around a circumference of the removable part and configured to cause a fluid to flow from an inlet port towards the filter that is disposed inside the removable part; and an outlet channel spaced apart from the inlet channel, extending around the circumference of the removable part, and configured to cause a filtered fluid to flow from the filter to an outlet port of the single assembly. Accordingly, the aquatic robot may be further configured to autonomously decouple the removable part from the stationary part, replace the filter with another filter, and re-couple the removable part to the stationary part.

The aquatic robot also comprises a micro- or milli-fluidics system. The micro- or milli-fluidics system may comprise a 3D printed part that is configured to perform eDNA purification. The 3D printed part comprises at least one fluid channel configured to transport the lysate to mixing channel(s). Each mixing channel may have a spiral shape configured to facilitate mixing of the lysate with a cleaning solution. The 3D printed part may also comprise a fluid holding area that is sized and shaped to control a flow of the fluid to the mixing channel(s) based on a surface tension on the fluid and an internal pressure of the micro- or milli-fluidics system. The 3D printed part may be further configured to: allow the fluid to flow from the mixing channel(s) and through another filter configured to retain DNA; transport a release agent within the micro- or milli-fluidics system to the filter for releasing the purified eDNA therefrom; and/or transport the released purified eDNA out of the micro- or milli-fluidics system.

BRIEF DESCRIPTION OF THE DRAWINGS

The present solution will be described with reference to the following drawing figures, in which like numerals represent like items throughout the figures.

FIGS. 3A-3E (collectively referred to as "FIG. 3") provides illustrations that are useful for understanding the operations performed by the eDNA-bot shown in FIG. 1.

DETAILED DESCRIPTION

Figure 2:
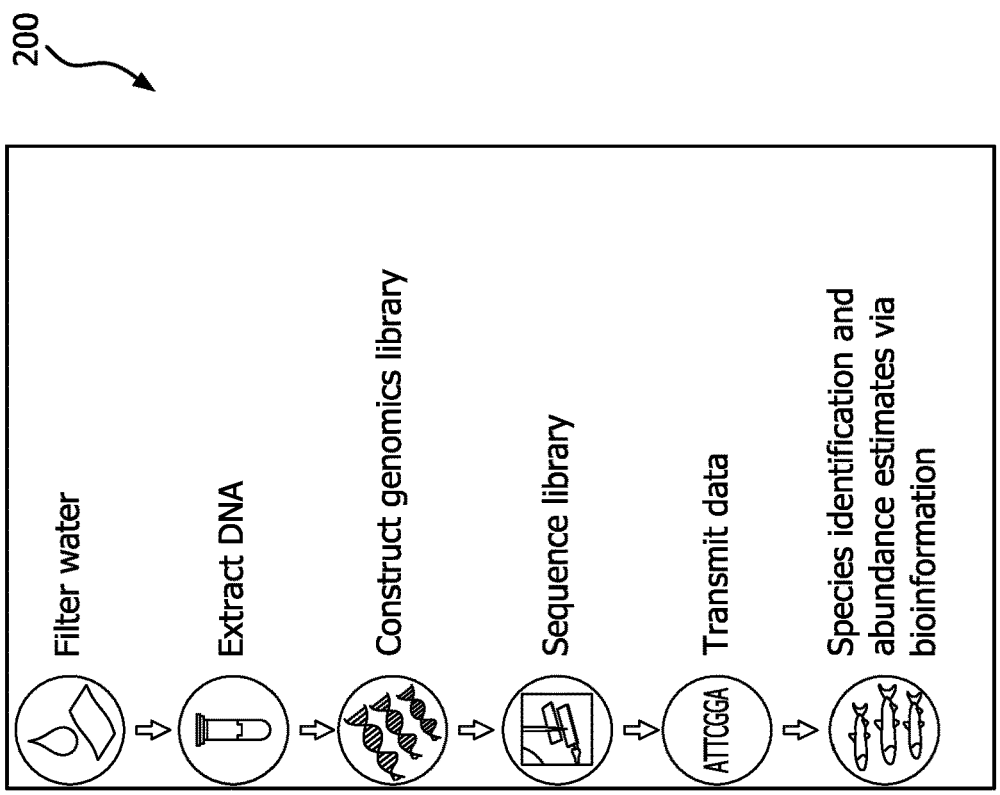
FIG. 2 provides an illustration of a system workflow.

Many of the biases in data generated using conventional biodiversity monitoring can be overcome by using environmental DNA (eDNA)—the tiny bits of DNA that are deposited into from the environment from organisms through normal sloughing of skin cells, spawning, waste excretion, and decomposition, etc.—that can be used to connect the genetic material in the environment to the physical presence and reltive abundance of species. Biodiversity monitoring using eDNA has the potential to transform management and stakeholder decision-making because it can quickly be collected in environmental samples such as water, substrate, or air filtration and identified to the species-level through analysis of the unique gene sequences. This species (or genus level) identification can be performed on-board by the aquatic robot or by a remote external device. In this way, eDNA has the potential for simultaneously assessing dynamics of single and multiple species, and surveying species composition and relative abundance that are important for monitoring at-risk, rare or protected species. Paired with recent innovations in high-throughput sequencing and bioinformatic infrastructure, the usage of eDNA is non-intrusive and cost-effective compared to conventional monitoring methods.

The vast majority of eDNA studies focus on targeting one rare, at-risk, or invasive species using quantitative PCR (qPCR) for detection. However, with advances in high-throughput sequencing and bioinformatics, the analysis of eDNA matured to using metabarcoding and metagenomics techniques. Metabarcoding targets a specific gene region (e.g., cytochrome oxidase I) in the environmental sample and with next-generation sequencing then produces all of the sequences in that sample at that region which can then be mapped back to individual species (or genus) and capture a comprehensive list of species (or genera) with a single sample. In contrast to metabarcoding of targeted regions of the genome, metagenomic approaches sequence all of the whole genomes present in a single environmental sample and additionally captures whole genome-wide nucleotide variations within a species enabling detection of population level estimates (e.g., population genetics), as well as emerging and new variants of pathogens.

Having real-time biodiversity data is important for conducting nimble biodiversity conservation and management actions that can be quickly informed and adapted to changing conditions, but the process from field sampling to sequence data acquisition, can take months to years depending on the scope of the study, and can increase the potential for sample contamination along the chain of custody. Moreover, time lags and potential contamination may provide a dated or incorrect understanding of what species are in an area which may lead to conservation and management plans that are obsolete before being enacted.

The present solution concerns a remote, autonomous eDNA laboratory that collects, processes, sequences and outputs eDNA sequence data. The eDNA laboratory is referred to herein as an eDNA-bot or an aquatic robot. The eDNA-bot enables real-time biodiversity assessments for rapid evaluation of conservation and management actions. The eDNA-bot eliminates hands-on sample processing that can introduce contamination and increase confidence and accuracy of results. The eDNA-bot can be used for, but is not limited to, detection, delineation, and abundance estimates of biodiversity, rare, threatened or endangered species, introduce and/or invasive species, pathogen detection in natural systems and man-made infrastructure (e.g., wastewater and aquaculture), healthcare, security, and/or defense.

Figure 1:
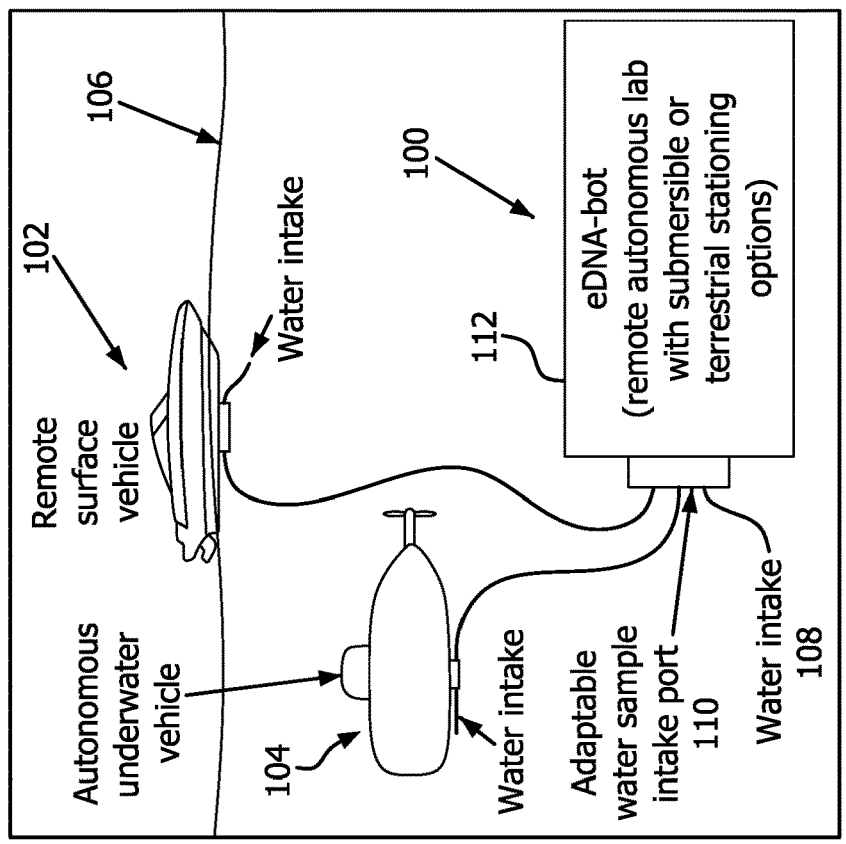
FIG. 1 provides an illustration of a system implementing the present solution.

FIG. 1 provides an illustration showing the eDNA-bot 100 deployed in a body of water 106 along with a remote surface vehicle 102 and an autonomous underwater vehicle 104. The eDNA-bot 100 is a fully functional remote, autonomous eDNA sampler. The eDNA-bot 100 combines microfluidics, ambient stable molecular reagents, an off-the-shelf genome sequencer, and telemetry to encompass the entire eDNA workflow 200 (shown in FIG. 2) from sample collection to data output providing eDNA results in real-time while reducing costs, contamination, and risk to humans.

The eDNA-bot 100 can be deployed for at least a month and is adaptable to specific user needs such as delineating the distribution of protected species, detecting new invasive species fronts, changes in community composition after a natural disaster, or identification of new zoonotic pathogens and emerging infectious disease. For example, contaminants and pathogens found in wastewater treatment facilities could be quantified in real-time and reduce exposure of personnel to potential harm. With next-generation sequencing capabilities, the eDNA-bot 100 could provide real-time monitoring of new pathogenic variants and guide human health policies focused on emerging disease (e.g., COVID-19).

The eDNA-bot 100 is configured to produce real-time sequencing data and results from eDNA. To do this, the eDNA-bot 100 begins with the collection of water samples using either a surface water collection vehicle 102, an underwater vehicle 104 and/or a stationary benthic water collection tube 108. Each of the listed components 102, 104, 108 connect to and are pumped into a sample intake port 110 on a main body 112 of eDNA-bot 100. The main body 112 may, for example, have an overall size that is the same as or similar to the size of a fifty gallon drum.

FIG. 3 provides illustrations that are useful for understanding the operations performed by the eDNA-bot 100. A user is able to specify the volume of water to be sampled. Next as shown in FIG. 3A, an internal pump 302 pumps a sample 304 of water into the main body 112 of the eDNA-bot 100 and causes the sample to pass through a single-use filter 306. Any eDNA 308 in the sample 304 is retained in the filter 306.

Figure 3B:
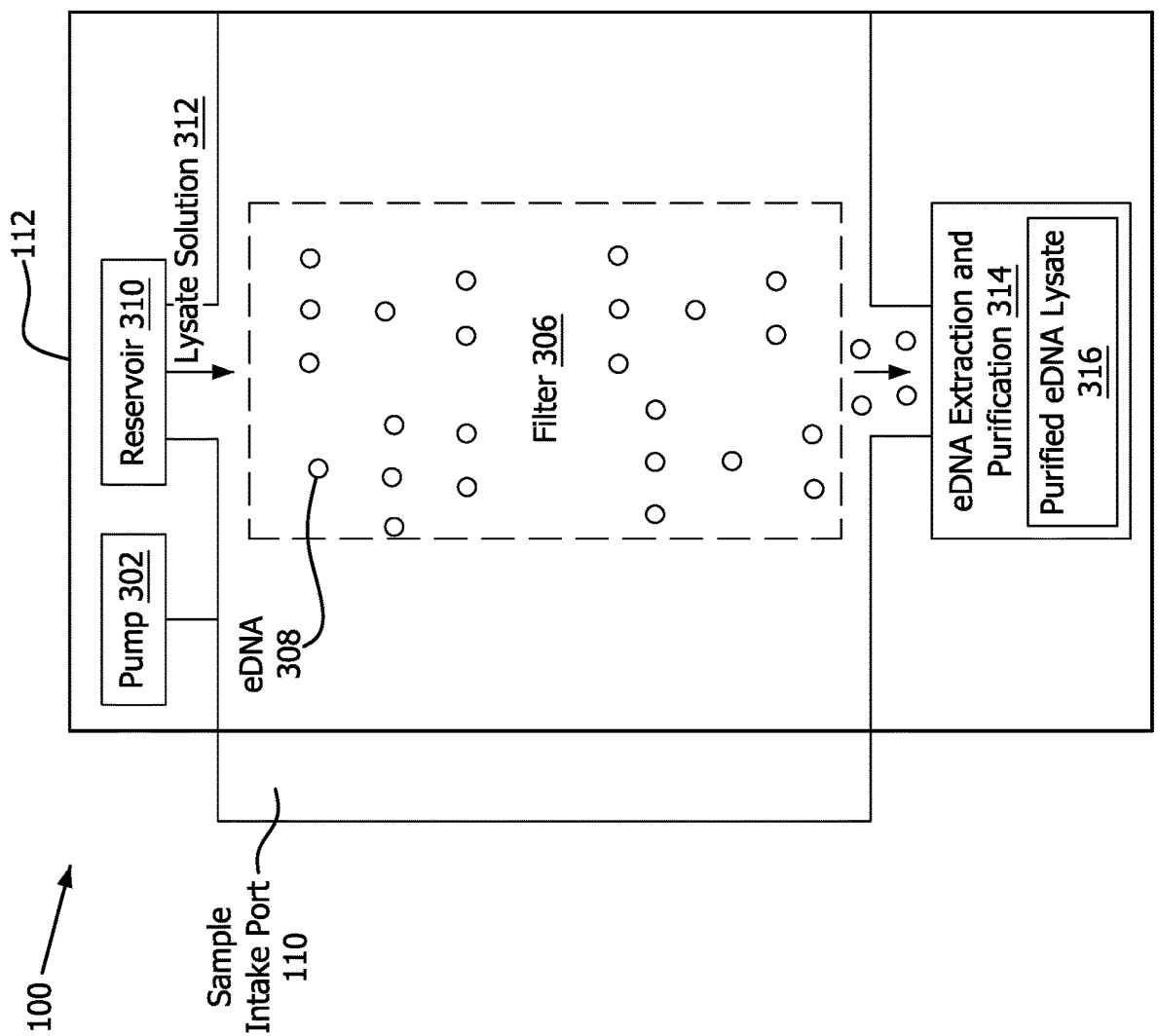
Figure 3C:
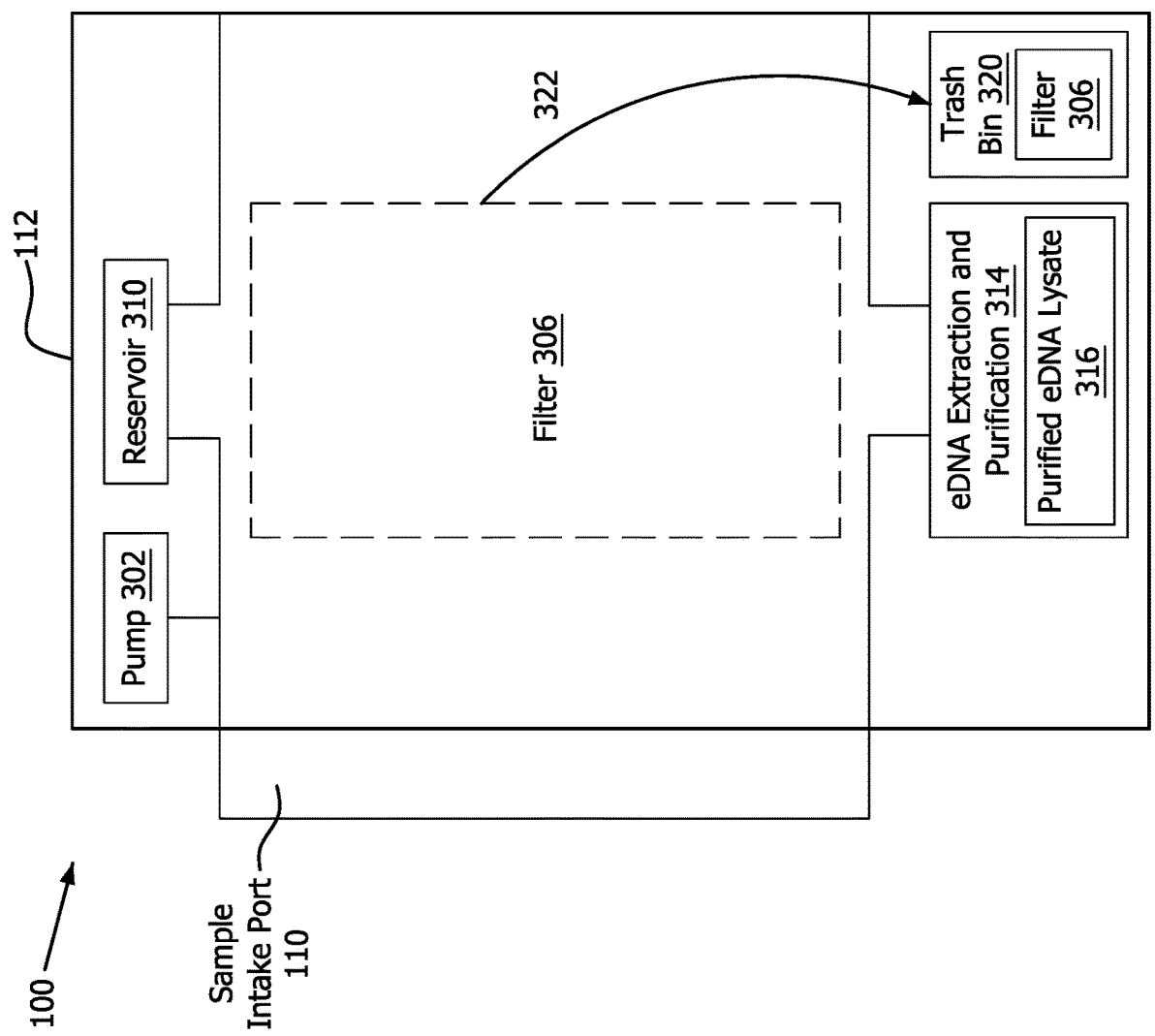

With reference to FIG. 3B, the eDNA-bot 100 comprises a reservoir 310 filled with a cell lysis solution 312. The lysis solution 312 is transferred to the filter 116 and heated so that cellular components are lysed and the eDNA 308 is released from the filter 306. The single-use filter 116 is then ejected into a trash bin 320 as shown by arrow 322 of FIG. 3C.

Figure 3D:
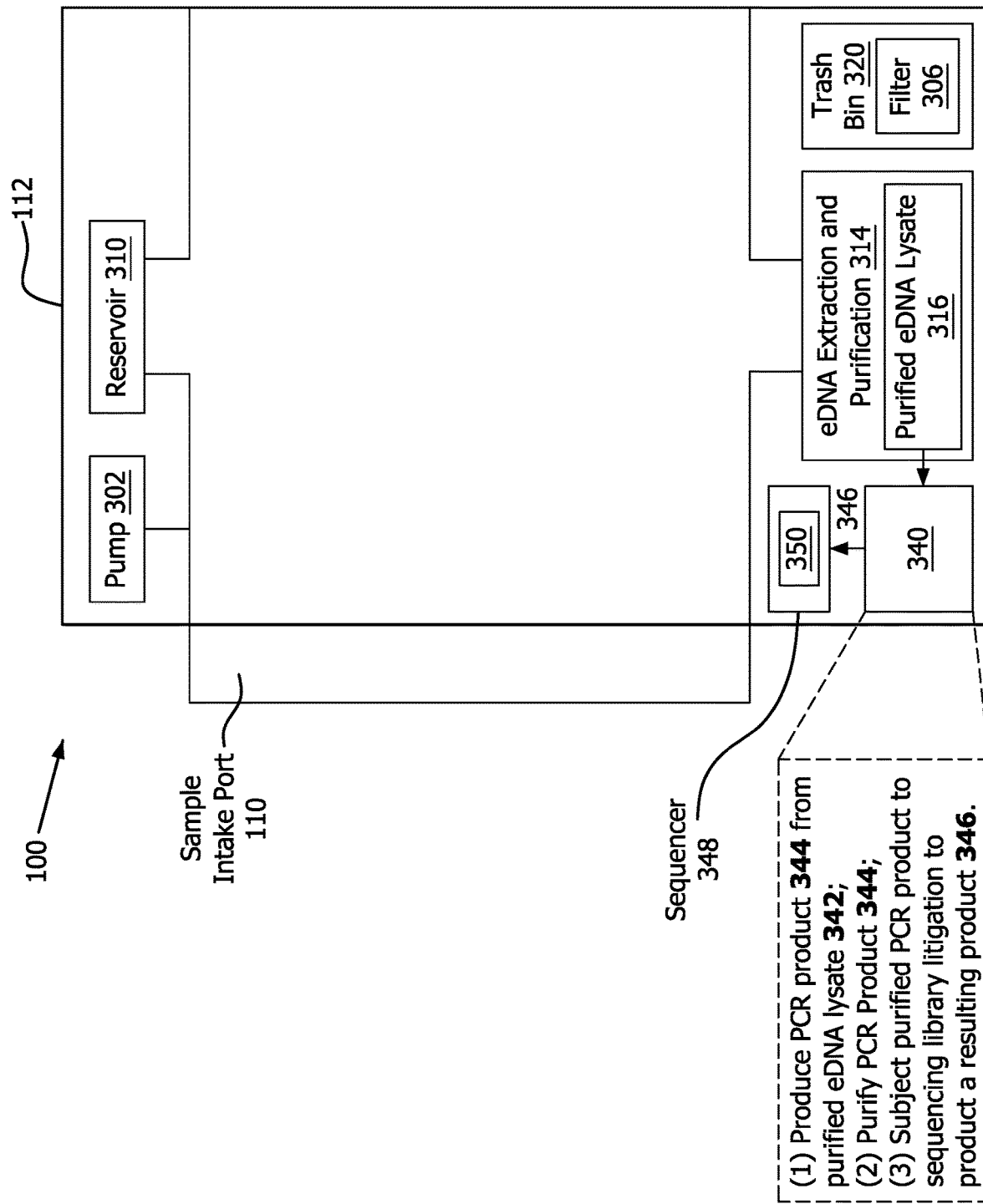
Figure 3E:
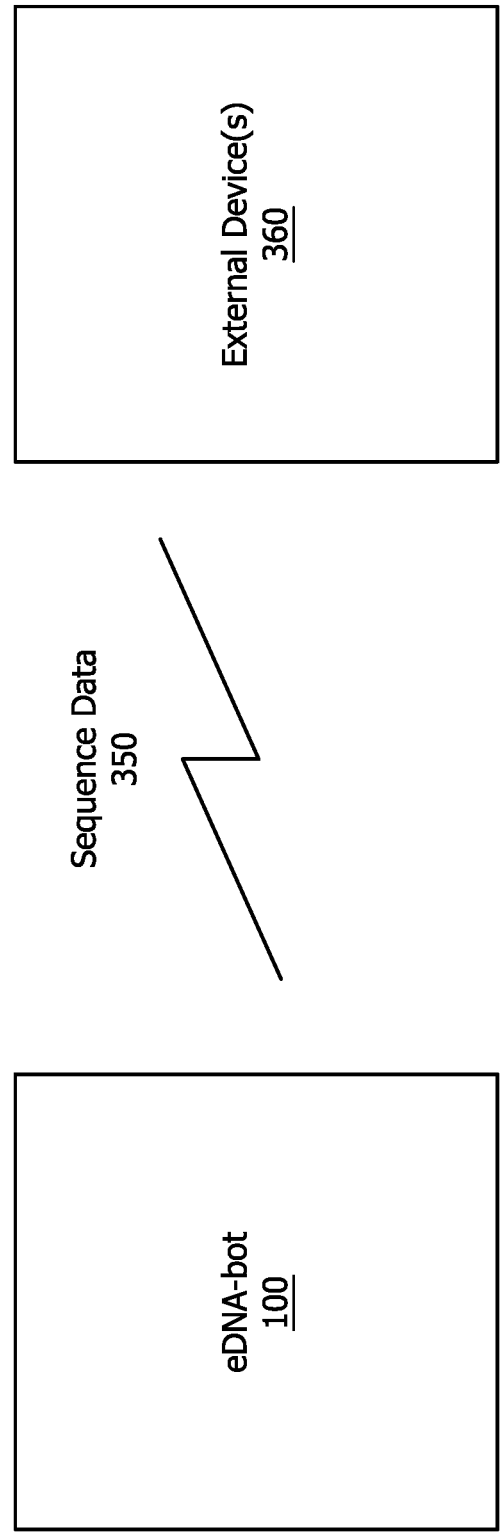

In FIG. 3D, the eDNA lysate 316 is provided to a device 314. At device 314, the following operations of FIG. 3E are performed: (i) a series of washing operations are performed using user-preferred buffer solutions to produce purified eDNAse 316. The purified eDNA is then transferred to another device that: (1) amplifies the purified eDNA 316 with a polymerase chain reaction (PCR) with user-defined primers and shelf-stable molecular reagents to produce a PCR product 344; (2) purifies the PCR product 344 with a wash solution in combination with magnetic beads; (3) subjects the purified PCR product to sequencing library ligation to produce a resulting product 346. The resulting product 346 is transferred to a sequencer 348. At the sequencer 348, the eDNA is sequenced using the resulting product 346 to produce sequence data 350. The sequence data 350 is transmitted from the eDNA-bot 100 to external device(s) 360 as shown in FIG. 3E.

This entire process of FIGS. 3A-3E can take place within a few hours' time and allow for repeat environmental samples to be collected across day(s), week(s), or month(s). The eDNA-bot 100 can be deployed for months at a time depending on the shelf-life (e.g., an average 1-3 months), type, and amount of reagents to be used and stored in eDNA-bot at ambient temperature. The eDNA-bot 100 can conduct single species, metabarcoding, and metagenomics analysis based on user preferences. The integration of a full eDNA processing pipeline in the eDNA-bot 100 elevates the application of eDNA across organismal types and sectors (e.g., hydropower environmental assessments, biodiversity assessments for conservation, waste-water treatment to track emerging diseases and zoonotic pathogens) while also reducing timing, costs, and hazardous exposure.

Figure 4:
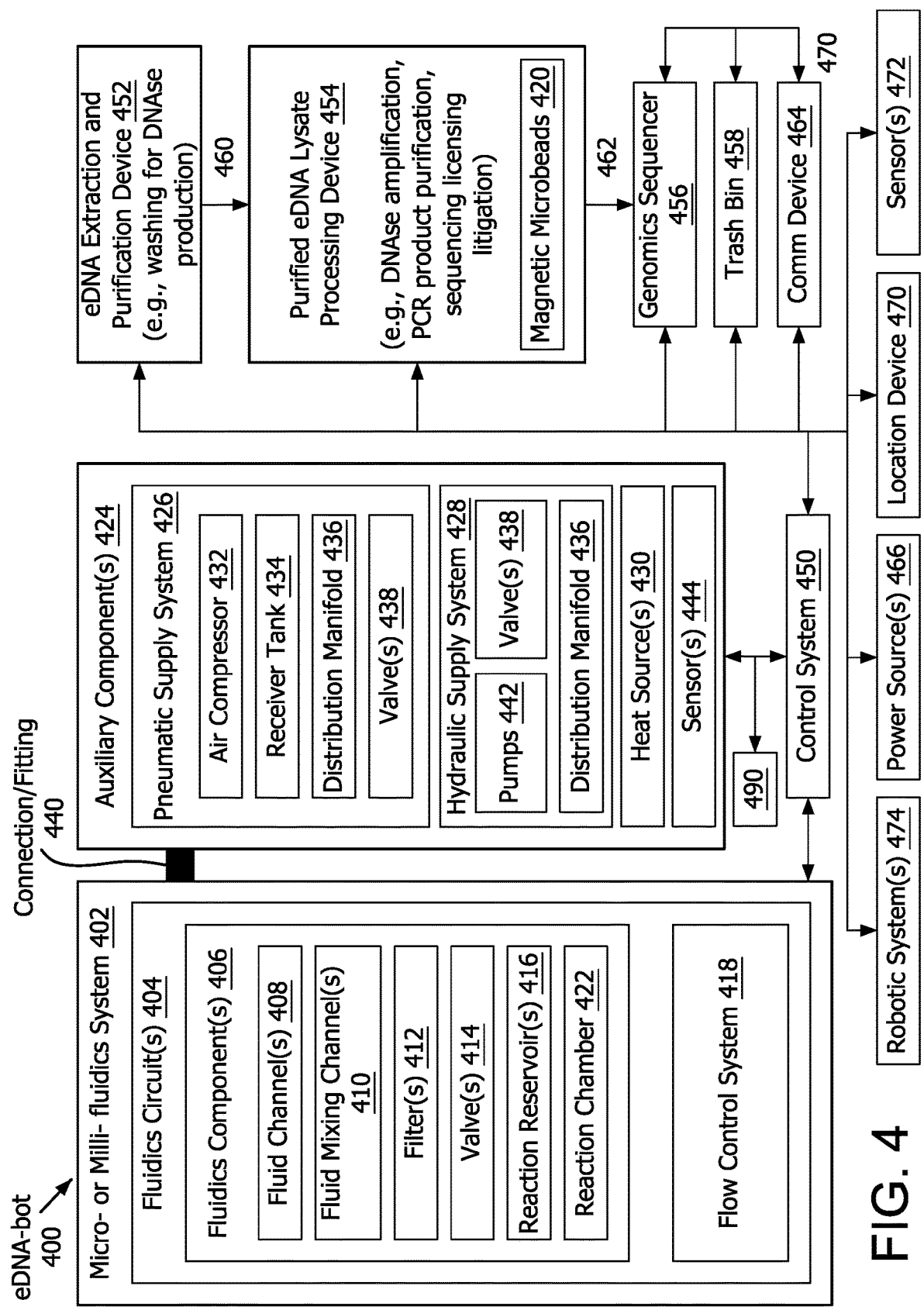
FIG. 4 provides a detailed block diagram of an illustrative eDNA-bot.

FIG. 4 provides a more detailed block diagram of an eDNA-bot 400. The eDNA-bot 100 of FIG. 1 can be the same as or similar to eDNA-bot 400. As such, the discussion of eDNA-bot 400 is sufficient for understanding eDNA-bot 100 of FIG. 1. eDNA-bot 400 is an autonomous watercraft with a propulsion system 490. Propulsion system 490 is configured to generate thrust to move the watercraft through a body of water (e.g., a lake or the ocean). Any known or to be known propulsion system can be used here. For example, the propulsion system comprises an engine, motor(s), gear(s), propeller(s) and/or other mechanisms.

The eDNA-bot 400 is configured to remotely and autonomously filter water from an environment (e.g., wastewater), extract DNA, amplify and sequence DNA, and then transmit the sequence data via some telemetry system to a remote device. The remote device can include, but is not limited to, a computing device executing bioinformatics pipeline software operative to identify species from an eDNA sample. Settings of the eDNA-bot 400 can also be changed remotely using the remote device and the bioinformatics pipeline software. The eDNA-bot 400 can be used in various applications. Such applications include, but are not limited to: monitoring of biological communities; monitoring and detection of rare, threatened, endangered, and invasive species; monitoring and detection of known pathogens in wastewater; monitoring and detection of emerging pathogens and their variants in wastewater; and/or monitoring for biological agents in water supplies.

The eDNA-bot 400 comprises a micro- or milli-fluidics system 402. The fluidics system 402 improves the overall space and power requirements, reliability, time, cost, and ease of use in processing eDNA samples for aquatic biomonitoring applications. The eDNA-bot 400 is configured to provided controlled flow of a fluid and/or magnetic microbeads through the fluidics system 402. The fluidics system 402 is designed to encompass the entirety of the eDNA-bot pipeline by combining various elements and components as noted below. In some scenarios, a monolithic design for the fluidics system 402 may be designed such that the entire system can be 3D printed at one time. In other scenarios, if more than one 3D print is required, the number of prints may be minimized to minimize the number of components.

The fluidics system 402 comprises fluidics circuits 404 with fluidics components 406. The fluidics components 406 can include, but are not limited to, fluid channel(s) 408, fluid mixing channel(s) 410, filter(s) 412, valve(s) 414, and/or reacting reservoir(s) 416. The listed fluidics components may be additively manufactured, printed using a stereolithography (SLA) 3D printer, and/or 3D printed using vat polymerization. The designs of the fluidics components 406 and the printing parameters can be adjusted in order to optimize the performance of the fluidics components. The performance of the fluidics components 406 can be based on the specific part. For example, the performance of the fluid channels 408 is measured by resistance to flow, the performance of fluid mixing is observed by how well two fluids are mixed, and the performance of valves is based on leakage and reaction speed. The present solution is not limited to the particulars of this example.

A flow control system 418 is provided to manipulate the movement of magnetic microbeads 420 within the fluidic system 402. The magnetic microbeads 420 are transported through fluid channels 408 using fluid flow. The magnetic microbeads 420 are captured within the reaction chamber 422 using electromagnet(s) (not shown).

The eDNA-bot 400 also comprises auxiliary components 424. The auxiliary components 424 comprise a pneumatic supply system 426, a hydraulic supply system 428, and heat source(s) 430 for the reaction chamber 422. Systems 426, 428 are designed to be relatively compact with a manifold and valving system to direct the fluids to the proper locations. The pneumatic supply system 426 is configured to transport the fluid and/or agitate (or mix) the fluid. Accordingly, the pneumatic supply system 426 comprises an air compressor 432, a receiver tank 434, a distribution manifold 436, and control valves 438. A connection/fitting 440 is provided to attach to the pneumatic supply system 426 to the fluidics system 402. The hydraulic supply system 428 comprises pumps 442 to pump the various different liquids needed to perform the chemistry. Systems 426, 428 are connected to a control system 450.

Control system 450 is configured to autonomously control operations of components 432, 438, 442 and 430 of systems 426, 428. The heat source(s) 430 may be controlled with a closed loop control system to ensure that the temperature in the reaction chamber 422 remains stable without affecting the other regions of the fluidics system 402. Sensor(s) 444 is(are) provided to facilitate the closed loop control and/or monitoring of the reaction chamber temperature. The control valve(s) 438 and/or other valve(s) can be selectively caused by the control system 450 to transition between open positions and closed positions.

Control system 450 is also connected to an eDNA extraction and purification device 452, a purified eDNA lysate processing device 454, a genomics sequencer 456, a trash bin 458, and a communication device 464. Components 454, 456, 458, 464 may include, but are not limited to, commercial-off-the-shelf (COTS) items. For example, the eDNA lysate processing device 454 can include a VoITRAX® device, while the sequencer 456 includes a MinION® device. The present solution is not limited in this regard. The control system 450 facilitates automation of the molecular steps of the workflow including loading the genomic libraries into the sequencer 456 and operations of the listed components (e.g., eDNA extraction, purification and PCR amplification).

Figure 5:
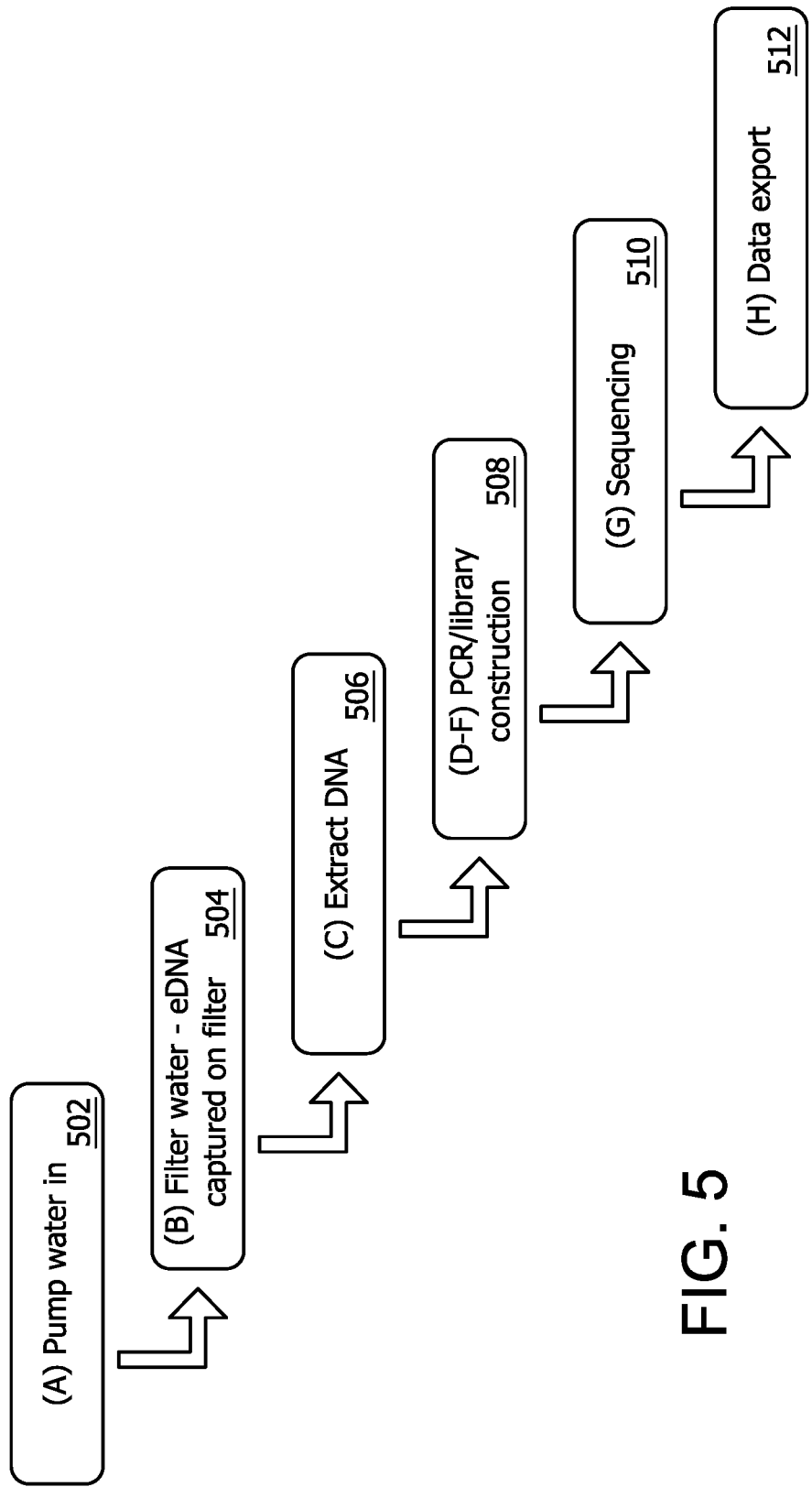
FIG. 5 provides an illustration of a system workflow for the eDNA-bot shown in FIG. 4.

Operations of the eDNA-bot 400 will now be discussed in relation to FIG. 4 and FIG. 5. During operations, water is pumped into the eDNA-bot 400 as shown by block 502. The water is filtered in block 504. The filter(s) 412 is(are) used to capture eDNA from a sample of water input into the fluidic system 402.

Next, in block 506 the eDNA is extracted. This eDNA extraction is achieved using a lysis solution which is heated on the filter(s) 412 so that the cellular matrices are lysed and eDNA is released therefrom. The filter(s) 412 may be ejected by robotic system(s) 474 (e.g., an articulating arm or other mechanical means) into a trash bin 458 once the eDNA lysate is released and provided to the eDNA extraction and purification processing device 452. The purified eDNA lysate is then transferred to the purified eDNA lysate processing device 454.

As shown by block 508, the device 454 performs the following operations: amplify purified eDNA to produce a PCR product; purify the PCR product with a wash solution in combination with the magnetic beads 420; and subject the purified PCR product to sequencing library ligation to produce a resulting product 462. The resulting product 462 is transferred to a sequencer 456.

In bock 510, the sequencer 456 sequences the eDNA using the resulting product 462 to produce sequence data 470. The sequence data 470 is provided from the sequencer 456 to a communication device 464.

In block 512, the communication device 464 communicates the sequence data 470 to external device(s) 360. This communication can be wired and/or wireless. Any known or to be known wired and/or wireless communication technology can be used here.

Referring again to FIG. 4, the eDNA bot 400 is supplied power from power source(s) 466. Power source(s) 466 can comprise rechargeable power source(s), replaceable power source(s), portable power source(s), and/or energy harvesting based power source(s). For example, the powers source (s) can include a diesel generator and/or a solar harvesting circuit. The eDNA bot 400 may be designed with a housing (i) rugged enough to withstand inclement weather and being outdoors for months at a time and/or (ii) configured to facilitate easy transport (e.g., via mounting on a trailer).

Control system 450 may execute machine learning software to facilitate autonomous operations of the eDNA bot 100. The machine learning application 526 implements Artificial Intelligence (AI) that provides the eDNA-bot 400 with the ability to automatically learn and improve operations from experience without being explicitly programmed. The machine learning application employs one or more machine learning algorithms that learn various information from accessed data (e.g., via pattern recognition and prediction making). Machine learning algorithms are well known in the art, and therefore will not be described herein in detail. Any known or to be known machine learning algorithm can be used herein without limitation. For example, in some scenarios, the machine learning application employs a supervised learning algorithm, an unsupervised learning algorithm, and/or a semi-supervised algorithm. The machine learning algorithm(s) is(are) used to model autonomous decisions based on data analysis (e.g., captured images, environmental information, and other information). For example, the machine learning algorithm learns over time what times of day and/or what locations in a body of are best for taking samples. This learning can be based on, for example, accuracy and/or validation of eDNA sequencing data and/or particulars of eDNA molecules specified by the eDNA sequencing data.

For example, the learning algorithm(s) is(are) configured to: use sensor data received from sensor(s) 472 to detect or otherwise determine environmental condition(s) (e.g., weather, heat, humidity, water condition (e.g., clean or dirty due to storm); use sensor data received from sensor(s) 444 to detect or otherwise determine operational states of internal components (e.g., detect operational faults, malfunction or damage to internal component that might require service or repair); optionally return to a docking station based on results from processing sensor data (e.g., system fault, malfunction or damage); and/or optionally cause the eDNA-bot to take an action based on spatial awareness and/or situational awareness. The spatial awareness and/or situational awareness can be facilitated by a location device 470 (e.g., a GPS device). Sensor(s) 472 can include, but are not limited to, water detectors, accelerometers, camera(s), radar device(s), lidar device(s), microphone(s) and/or proximity sensor(s). The spatial and/or situational awareness can assist the eDNA-bot with obstacle avoidance and/or sample collection at multiple different locations (which may be preselected or randomly selected) within a given geographic area.

Figure 6:
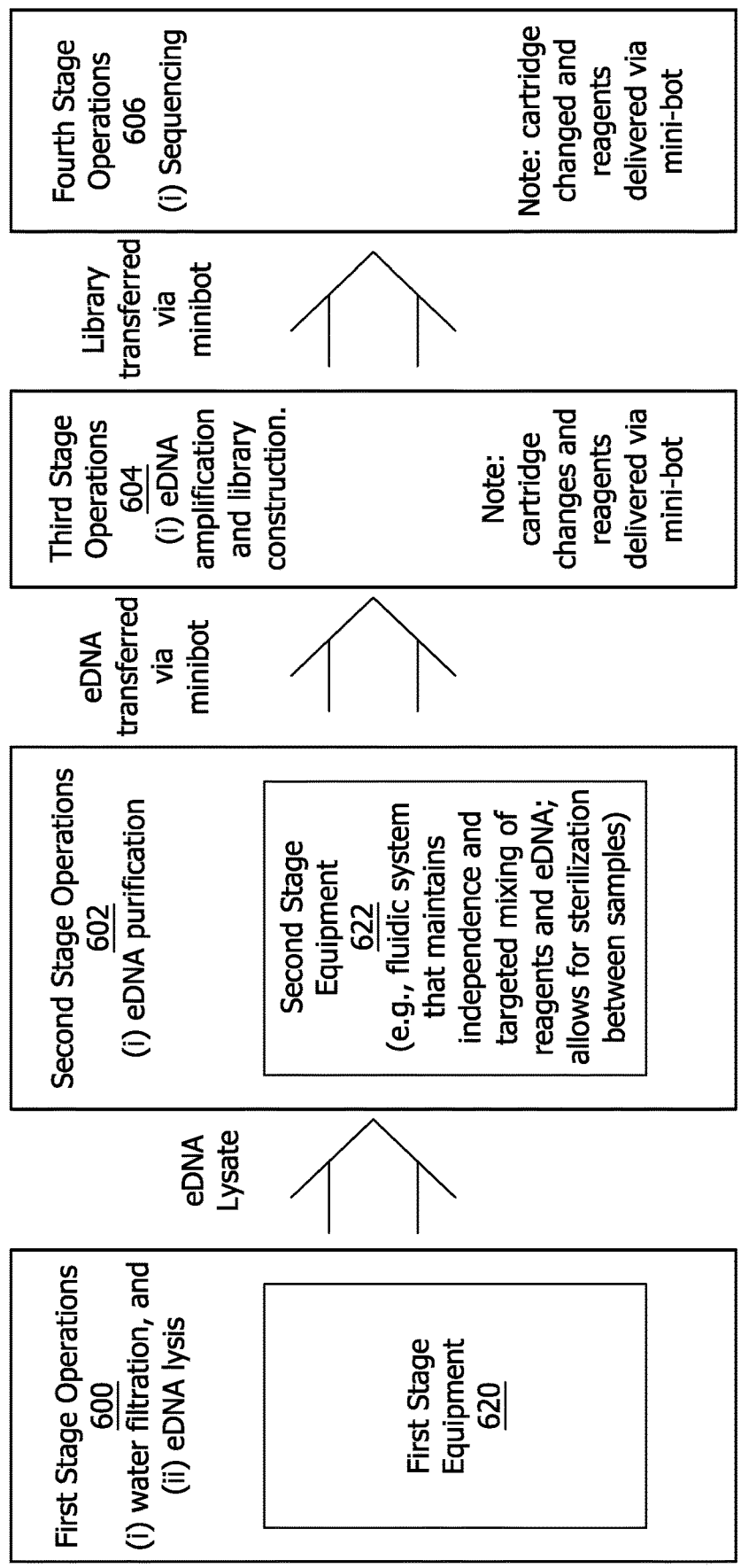
FIG. 6 provides an illustration that is useful for understanding operations of the eDNA-bot of FIG. 4.
Figure 7:
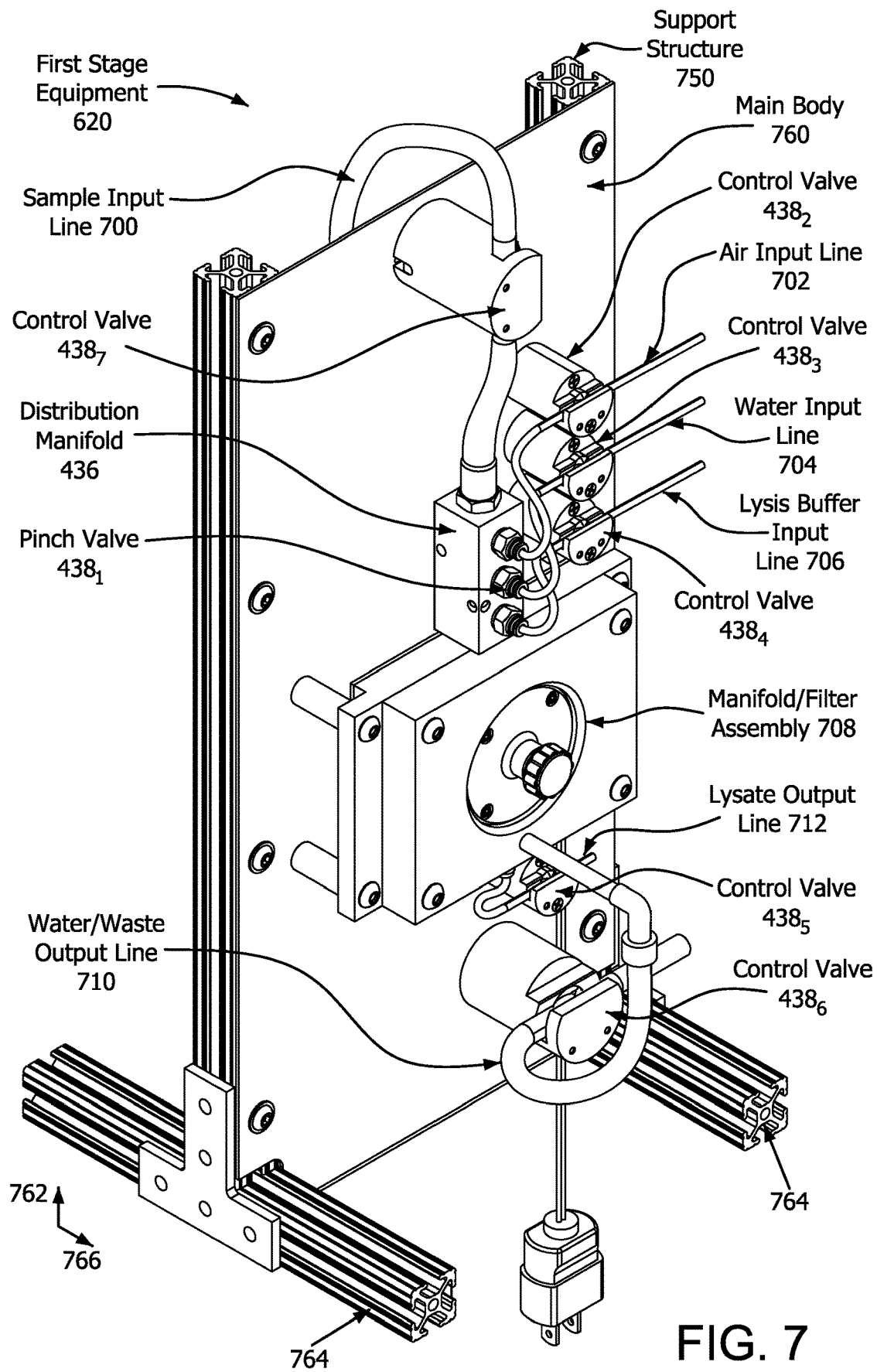
FIGS. 7-8 each provides a front perspective view of a water filtration and eDNA lysis device.
Figure 8:
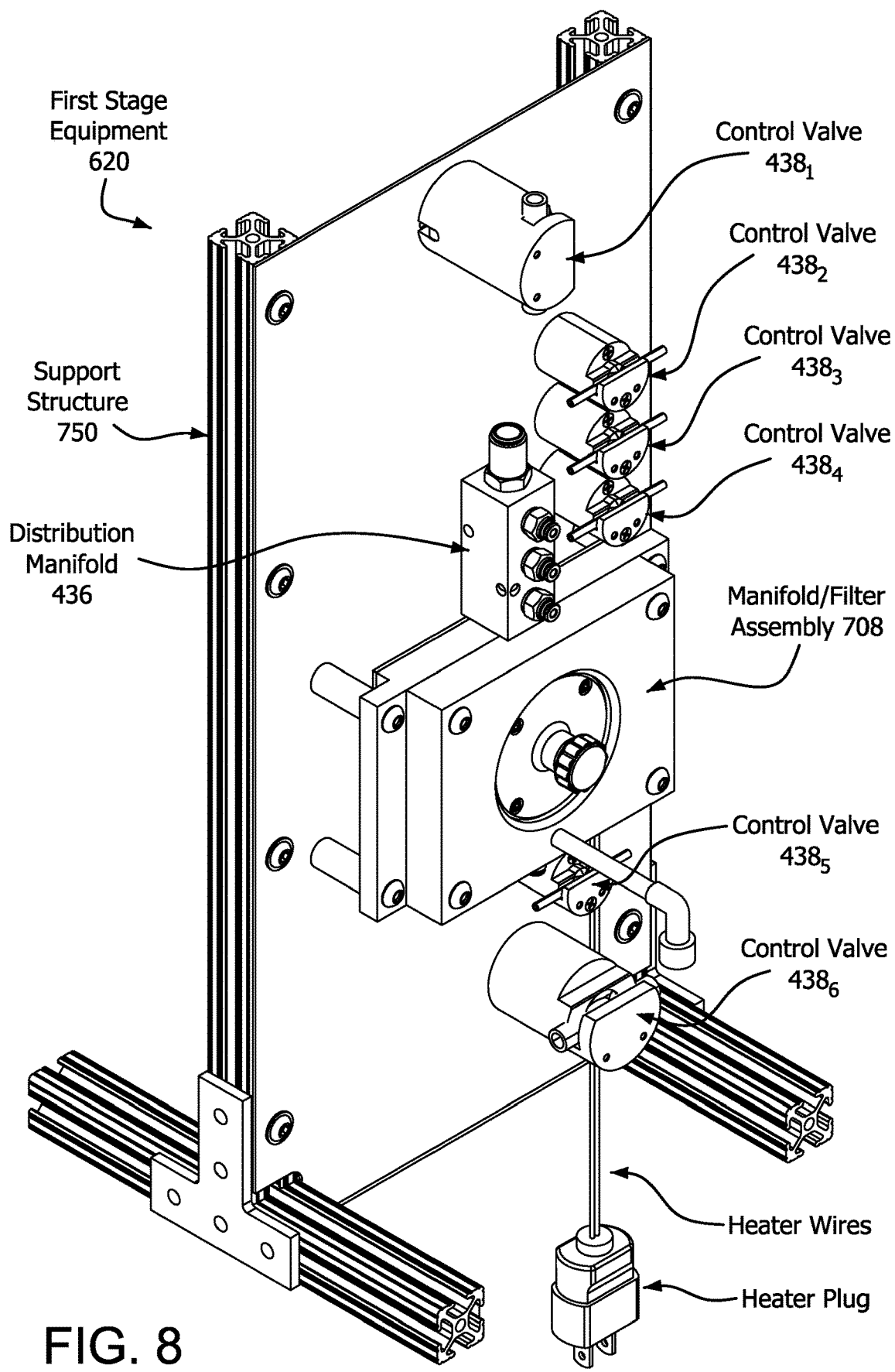

FIG. 6 provides an illustration that is useful for further understanding the operations of the eDNA-bot 400. In FIG. 6, the operations implemented by the eDNA-bot 400 include: first stage operations 600 performed by the fluidics system 402 that involve water filtration and eDNA lysis; second stage operations 602 that are performed by the eDNA extraction and purification device 452; third stage operations 604 performed by the purified eDNA lysate processing device 454 that involve DNA amplification and library construction; and fourth stage operations 606 that are performed by the sequencer 456 that involve sequencing. The first stage operations 600 are implemented using novel first stage equipment 620 which will be discussed in detail below in relation to FIGS. 7-10. The second stage operations 602 are implemented using novel second stage equipment 622 which will be discussed in detail below in relation to FIG. 11. As noted above, the purified eDNA lysate processing device 454 and/or sequencer 456 can include COTS device(s).

Referring now to FIGS. 7-10, there are provided illustrations of the first stage equipment 620 which implements the fluidics system 402 and the eDNA extraction and purification device 452 of FIG. 4. First stage equipment 620 comprises a support structure 750 configured to structurally support valves 414, distribution manifold(s) 436, and a manifold/filter assembly 708. The support structure 750 can include a main body 760 that extends in a vertical direction 762 and is maintained in the vertically extending state by members 764. Members 764 extend in a horizontal direction 766, and therefore are angled relative to the main body 760. Members 764 may be arranged so as to extend perpendicular to the main body 760.

The valves 438 include pinch valves $438_1$ and control valves $438_2$-$438_7$. Control valve $438_7$ is provided to control the flow of a water sample from the environment into the distribution manifold 436. Control valve $438_2$ is provided to control fluid flow from air compressor 432 through an air input line 702 into the distribution manifold 436. Control valve $438_3$ is provided to control fluid flow from a pump 442 (not shown in FIGS. 7-10) through a water input line 704 into the distribution manifold 436. Control valve $438_4$ is provided to control fluid flow through a lysis buffer input line 706 into the distribution manifold 436. Control valve $438_5$ is provided to control the flow of eDNA lysate through the lysate output line 712. Control valve $438_6$ is provided to control the flow of fluid out of the manifold/filter assembly 708 and through the water/waste output line 710. Operations of valves 438 are controlled by control system 450 of FIG. 4.

Figure 9:
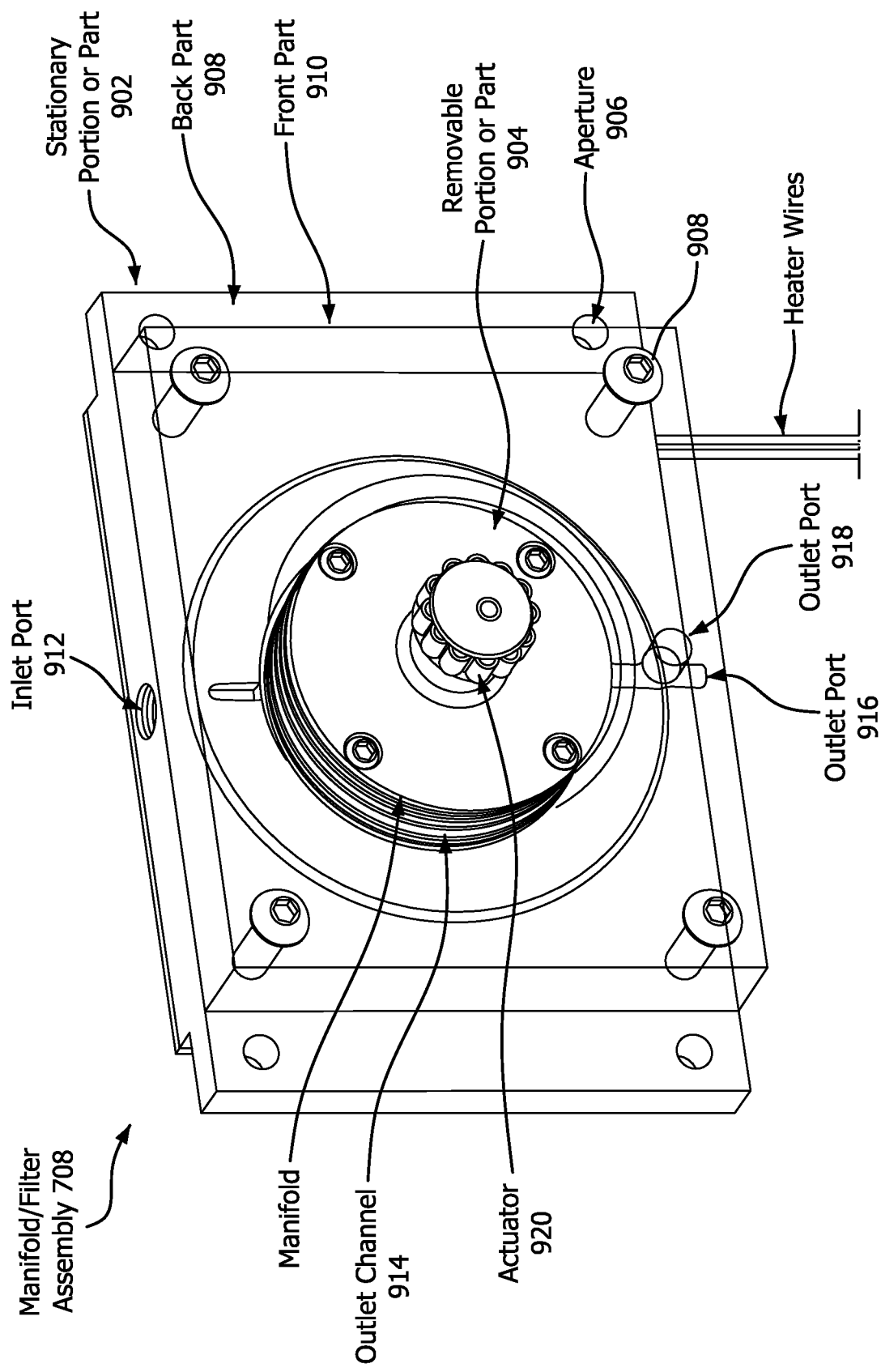
FIG. 9 provides a front perspective view of an assembly in which a manifold and filtration system are integrated with each other.
Figure 10:
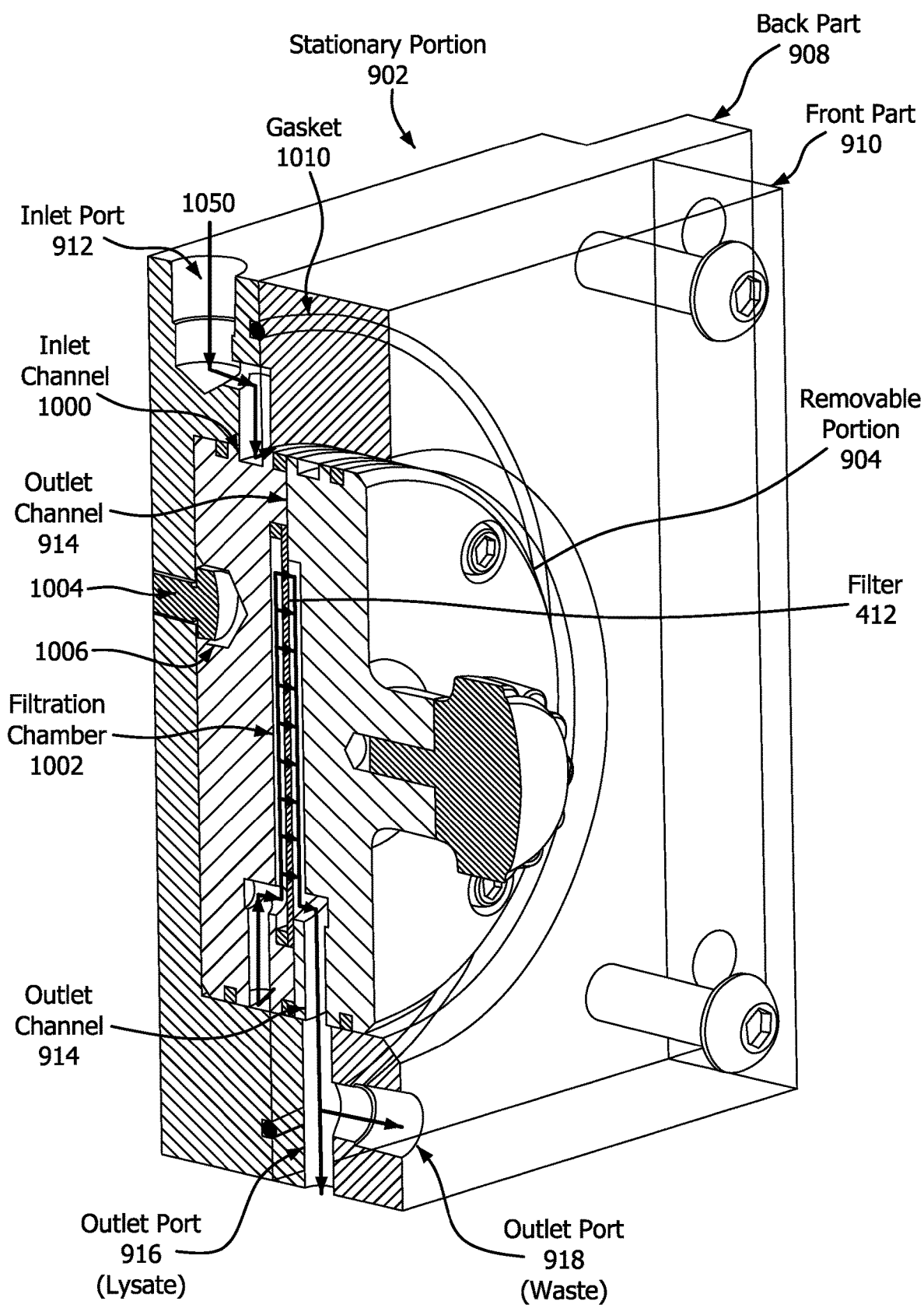
FIG. 10 provides a cross-sectional view of the assembly shown in FIG. 8.

The manifold/filter assembly 708 includes a part in which a manifold is integrated with a filter assembly in a manner that allows for relatively quick and easy replacement of the filter. A front perspective view of the manifold/filter assembly 708 is provided in FIG. 9. A cross-sectional view of the manifold/filter assembly 708 is provided in FIG. 10. As shown in FIGS. 9-10, the manifold/filter assembly 708 is formed of two halves, namely a stationary portion (or part) 902 and a removable portion (or part) 904. The stationary portion 902 is configured to be securely coupled to the main body 760 of the support structure 750. This coupling can be achieved using any coupling means such as weld(s), adhesive(s), screw(s), and/or other mechanical couplers. In the screw scenario, screws are inserted into apertures 906 formed through the stationary half 902 and into threaded holes of the main body 760 of the support structure 750. The threaded engagement of the screw(s) with the threaded holes secures the stationary half 902 to the support structure 750.

The stationary portion 902 comprises a back part 908 and a front part 910 which have a gasket 1010 disposed therebetween. Gasket 1010 is compressed between the two parts 908, 910 to provide an environmental seal so that fluid(s) and/or contaminant(s) cannot flow out of or into the manifold/filter assembly 708. An alignment member 1004 is provided to ensure that the removable portion 904 is properly aligned with the stationary portion 902 when in an assembled configuration as shown in FIGS. 9-10. The alignment member 1004 is sized and shaped to be received in a blind hole 1006 formed in the removable portion 904.

As more clearly visible in FIG. 10, an inlet port 912 is provided with the back part 908. The inlet port 912 provides a means to introduce fluid(s) into an inlet channel 1000 as shown by arrows 1050. The inlet channel 1000 is defined between the stationary portion 902 and the removable portion 904. The inlet channel 1000 extends around a circumference of the removable portion 904. The inlet channel 1000 is configured to cause the fluid(s) to flow around the removable portion 904 and into a filtration chamber 1002, as also shown by arrows 1050.

During operation, the fluid(s) flow(s) through a filter 412 as further shown by arrows 1050. After passing through the filter 412, the fluid(s) flow(s) into an outlet channel 914 and out of an outlet port 916, 918. The outlet channel 914 is defined between the stationary portion 902 and the removable portion 904. The outlet channel 914 extends around a circumference of the removable portion 904. Outlet port 916 provides a means for eDNA lysate to flow out of the manifold/filter assembly 708, while outlet port 918 provides a means for waste to flow out of the manifold/filter assembly 708.

Upon completion of collecting an eDNA sample and processing the sample in the filter to product eDNA lysate, the filter 412 may be replaced with another filter. A robotic system 474 may be configured to autonomously replace the filter. For example, the robotic system 474 comprises an articulating arm configured to grasp an actuator 920. The actuator 920 can be pulled, rotated or otherwise actuated to cause decoupling of the removable portion 904 from the stationary portion 902. The decoupled removable portion 904 can then be moved to a filter replacement area (not shown) where the articulating arm performs actions to replace the filter 412 with another filter. The removed filter can be disposed in the trash bin 458. The present solution is not limited to the particulars of this example. Other means for decoupling the removable portion 904 from the stationary portion 902 can be used. Such other means can include, but are not limited to, a knob. The removable portion 904 can be coupled to the stationary portion 902 by any coupling means selected in accordance with a given application. For example, the removable portion 904 can be frictionally or threadingly coupled to the stationary portion 902.

Figure 11:
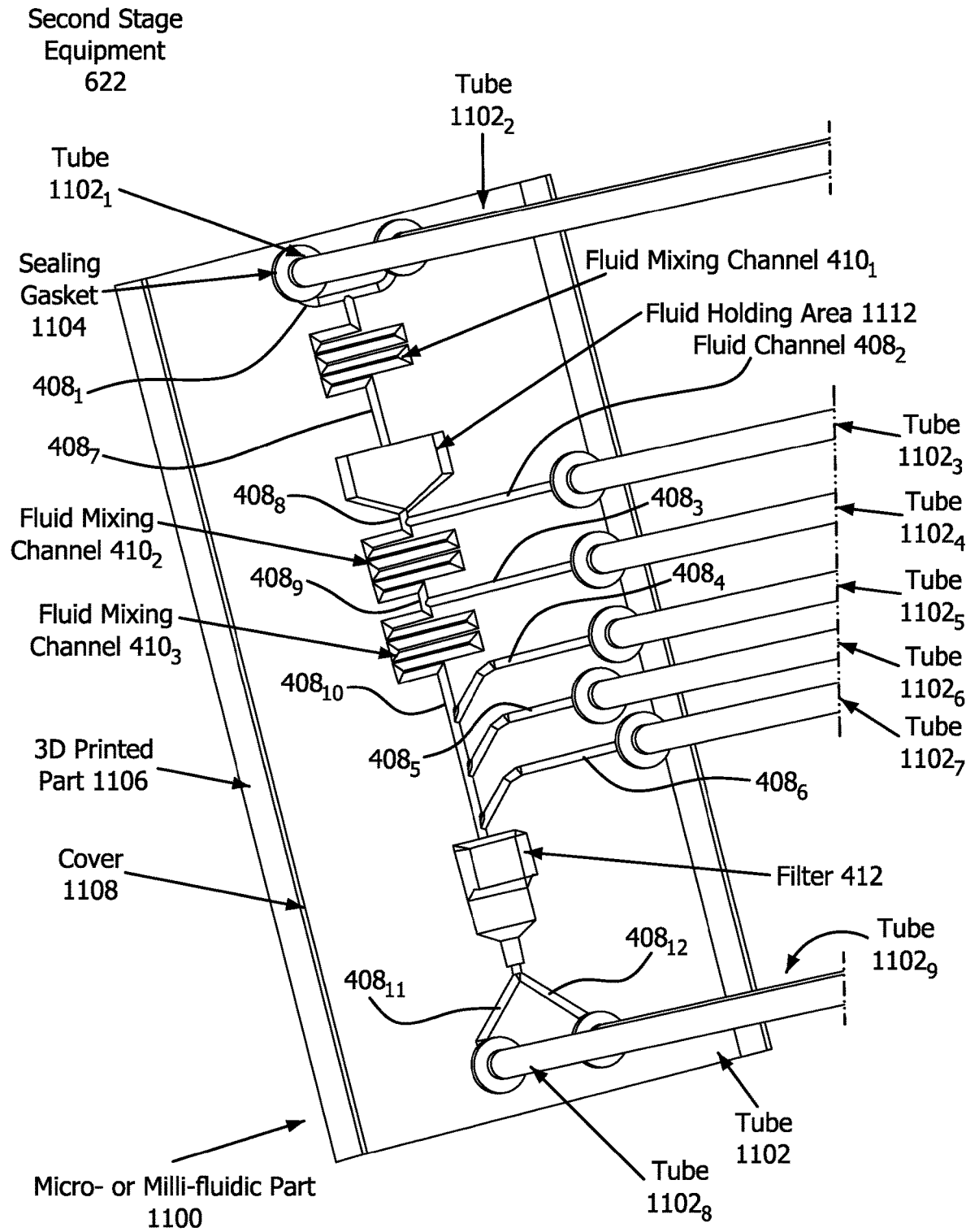
FIG. 11 provides a front perspective view of a micro- or milli-fluidic system.

FIG. 11 provides a front perspective view of the second stage equipment 622. The second stage equipment 622 is configured to implement operations of the eDNA extraction and purification device 452 that involve eDNA purification. Accordingly, the second stage equipment 622 comprises a micro- or milli-fluidic part 1100 to which a plurality of tubes 1102 can be coupled. A sealing gasket 1104 is provided to create a seal between a respective tube 1102 and the fluidic part 1100. The fluidic part 1100 comprises a 3D printed part 1106 and a cover 1108. The cover 1108 is formed of any material selected in accordance with a given application. Such material can include, but is not limited to, plastic. The sealing gaskets 1104 are compressed between the cover 1108 and the 3D printed part 1106.

The tubes 1102 include a first tube $1102_1$ for transporting a sterilization fluid, molecular grad water, and eDNA lysate independently from respective reservoirs (not shown in FIG. 11) to an inlet fluid channel $408_1$ of the fluidic part 1100. The sterilization fluid is first introduced to sterilize the fluidic part 1100. Next, the molecular grade water is introduced in the fluidic part 1100 via tube $1102_1$ to flush the system. Next, the eDNA lysate is introduced into the fluidic part 1100 via tube 1102$_1$. A second tube 1102$_2$ is provided for holding and transporting a mixing solution (to remove RNA contamination) from a respective reservoir (not shown in FIG. 11) to the inlet fluid channel 408$_1$ of the fluidic part 1100.

Other tubes 1102$_3$-1102$_6$ are provided for holding and transporting respective cleaning solutions from respective reservoirs (not shown in FIG. 11) to the fluidic part 1100. For example, tube 1102$_3$ transports a first cleaning solution from a reservoir (not shown in FIG. 11) to a fluid channel 408$_2$ of the fluidic part 1100. Tube 1102$_4$ transports a second cleaning solution (e.g., ethanol) from a reservoir (not shown in FIG. 11) to a fluid channel 408$_3$ of the fluidic part 1100. Tube 1102$_5$ transports a third cleaning solution from a reservoir (not shown in FIG. 11) to a fluid channel 4084$_3$ of the fluidic part 1100. Tube 1102$_6$ transports a fourth cleaning solution from a reservoir (not shown in FIG. 11) to a fluid channel 408$_5$ of the fluidic part 1100. Another tube 1102$_7$ is provided for holding and transporting a release solution from a reservoir (not shown in FIG. 11) to a fluid channel 408$_6$ of the fluidic part 1100. The cleaning solutions and release solutions can be selected in accordance with any given application. The cleaning solutions and release solutions can be obtained via COTS kits. The eDNA lysate is sequentially cleaned by the cleaning solutions which are pumped into the fluidic part 1100 via tubes 1102$_3$-1102$_6$. eDNA is released from the cleaned lysate via the release solution. The present solution is not limited to the particulars of this example. Any number of tubes and associated fluid channels can be provided in accordance with the given application.

A tube 1102$_8$ is provided for holding and transporting waste from an outlet fluid channel 408$_{11}$ of the fluidic part 1100 to a downstream system. Tube 1102$_9$ is provided for holding and transporting released eDNA from an outlet fluid channel 408$_{12}$ of the fluidic part 1100 to a downstream system. Other fluid channels 408$_7$-408$_{10}$ are provided. Fluid channels 408$_1$-408$_{12}$ are collectively referred to herein a fluid channels 408.

The fluid channels 408 are connected to a chain of other fluidics components 406. These other fluidics components 406 include fluid mixing channels 410$_1$, 410$_2$, 410$_3$ (collectively referred to as fluid mixing channels 410), a fluid holding area 1112, and a filter 412. Fluid mixing channel 410$_1$ is connected at an inlet end to inlet fluid channel 408$_1$ and connected at an outlet end to the fluid holding area 1112 via fluid channel 408$_7$. Fluid mixing channel 410$_2$ is connected at an inlet end to the fluid holding area 1112 via fluid channel 408$_8$ and is connected at an outlet end to fluid mixing channel 410$_3$ via fluid channel 408$_9$. Fluid mixing channel 410$_3$ is connected at an inlet end to fluid mixing channel 410$_2$ via fluid channel 408$_9$ and connected at an outlet end to filter 412 via fluid channel 408$_{10}$. Filter 412 is connected between the fluid mixing channel 410$_3$ and outlet fluid channels 408$_{11}$ and 408$_{12}$.

Each of the fluid mixing channels 410$_1$, 410$_2$, 410$_3$ comprises a circular cross-sectional profile and a spiral shape. The spiral shape can have any number of turns. The number of turns are selected in accordance with a given application. For example, as shown in FIG. 11, each fluid mixing channel 410$_1$, 410$_2$, 410$_3$ comprises five turns. The present solution is not limited in this regard. The fluid mixing channels 410$_1$, 410$_2$, 410$_3$ can have the same of different spring shape with the same or different number of turns.

In fluid mixing channel 410$_1$, the eDNA lysate is mixed with the mixing solution (to remove RNA contamination) transported via tube 1102$_2$ to the fluidic part 1100. The mixed solution is held in fluid holding area 1112 for a period of time. The period of time is a function of surface tension in the mixed solution and internal pressure of the fluidic part 1100. The surface tension and internal pressure prevent the mixed solution from flowing downstream for the period of time. Upon expiration of the period of time, the mixed solution flows downstream through fluid channel 408$_8$ and into fluid mixing channel 410$_2$.

In fluid mixing channel 410$_2$, the mixed solution is cleaned via a first cleaning solution transported via tube 1102$_3$ to the fluidic part 1100. The mixed solution is then cleaned by a second cleaning solution in fluid mixing channel 410$_3$. The mixed solution is then passed through filter 412 which binds the eDNA and expels the waste through the fluid channel 408$_{10}$ and then passed through the outlet fluid channel 1102$_8$. The filter-bound eDNA is then further cleaned by third and/or fourth cleaning solutions sequentially passing through the fluid channels 408$_4$ and 408$_5$, and deposited and expelled through the filter 412 through the fluid channel 408$_{10}$ and then passed through the outlet fluid channel 1102$_8$. The filter-bound eDNA is then washed with a releasing solution transported to the fluidic part 1100 via tube 1102$_7$ and the resulting purified eDNA (the released supernatant) passed through the fluid channel 408$_{12}$ to the outlet fluid channel 1102$_9$.

The pumps for pumping the fluids into the fluidic part 1100 are controlled by control system 450 of FIG. 4. The flow of the solutions in the fluidic part 1100 is controlled by the flow control system 418 of FIG. 4 which includes the fluid holding area 1112.

FIG. 12 provides a flow diagram of an illustrative method 1200 for operating an aquatic robot (e.g., eDNA-bot 100 of FIG. 1 and/or 400 of FIG. 4). Method 1200 begins with 1202 and continues with 1204 where the aquatic robot is autonomously propelled through a body of water to a location where a water sample is to be obtained. The aquatic robot collects a water sample at the location, as shown by block 1206. In block 1208, the water sample is caused to flow through a filter (e.g., filter 306 of FIG. 3 and/or filter 412 of FIG. 4) that retained eDNA. The eDNA is lysed and released from the filter resulting in an eDNA lysate product 1210.

In some scenarios, the filter is integrated with a manifold into a single assembly (e.g., manifold/filter assembly 708 of FIGS. 7-10). The assembly comprises: a stationary part (e.g., stationary portion or part 902 of FIG. 9); a removable part (e.g., removable portion or part 904 of FIG. 9) removably coupled to the stationary part; an inlet channel (e.g., inlet channel 1000 of FIG. 10) extending around a circumference of the removable part and configured to cause a fluid to flow from an inlet port (e.g., inlet port 912 of FIGS. 9-10) towards the filter (e.g., filter 412 of FIG. 4 and/or FIG. 10) that is disposed inside the removable part; and an outlet channel (e.g., outlet channel 914 of FIGS. 9-10) spaced apart from the inlet channel, extending around the circumference of the removable part, and configured to cause a filtered fluid to flow from the filter to an outlet port (e.g., outlet port 918 of FIG. 9) of the single assembly.

Referring again to FIG. 12A, method 1200 continues with 1212 where the eDNA lysate is processed to obtain a product for eDNA sequencing. The eDNA lysate is processed using a micro- or milli-fluidics system (e.g., fluidic system 402 and 452 of FIG. 4 and/or 622 of FIGS. 6 and 11) comprising a 3D printed part (e.g., 3D printed part 1106 of FIG. 11). The particulars of this eDNA lysate processing will be discussed here in relation to FIG. 12B. As shown by block 1252-1260 of FIG. 12B, this processing involves: using a surface tension on the fluid and an internal pressure of the micro- or milli-fluidics system to control a flow of the fluid from a fluid holding area (e.g., fluid holding area 1112 of FIG. 11) inside the micro- or milli-fluidics system to the mixing channel(s) (e.g., mixing channel(s) 410 of FIG. 4 and/or mixing channel(s) 410₁, 410₂ and/or 410₃ of FIG. 11); using a fluid channel (e.g., fluid channel(s) 408 of FIG. 4 and/or fluid channel(s) 408₈ and/or 408₉ of FIG. 11) of the micro- or milli-fluidics system to transport the lysate to the mixing channel(s) (wherein each mixing channel may have a spiral shape configured to facilitate mixing of the lysate with a cleaning solution); allow the fluid to flow from the mixing channel(s) and through another filter (e.g., filter 412 of FIG. 11) configured to retain DNA; transporting cleaning agents and a release agent within the micro- or milli-fluidics system to the filter for releasing the eDNA therefrom; and transporting the flow-through reagents, liquid waste, and released eDNA out of the micro- or milli-fluidics system. The released purified eDNA lysate is then transferred to the purified eDNA lysate processing device 454 of FIG. 4 and/or 604 of FIG. 6 to perform PCR amplification, PCR purification, and library ligation.

Figure 12A:
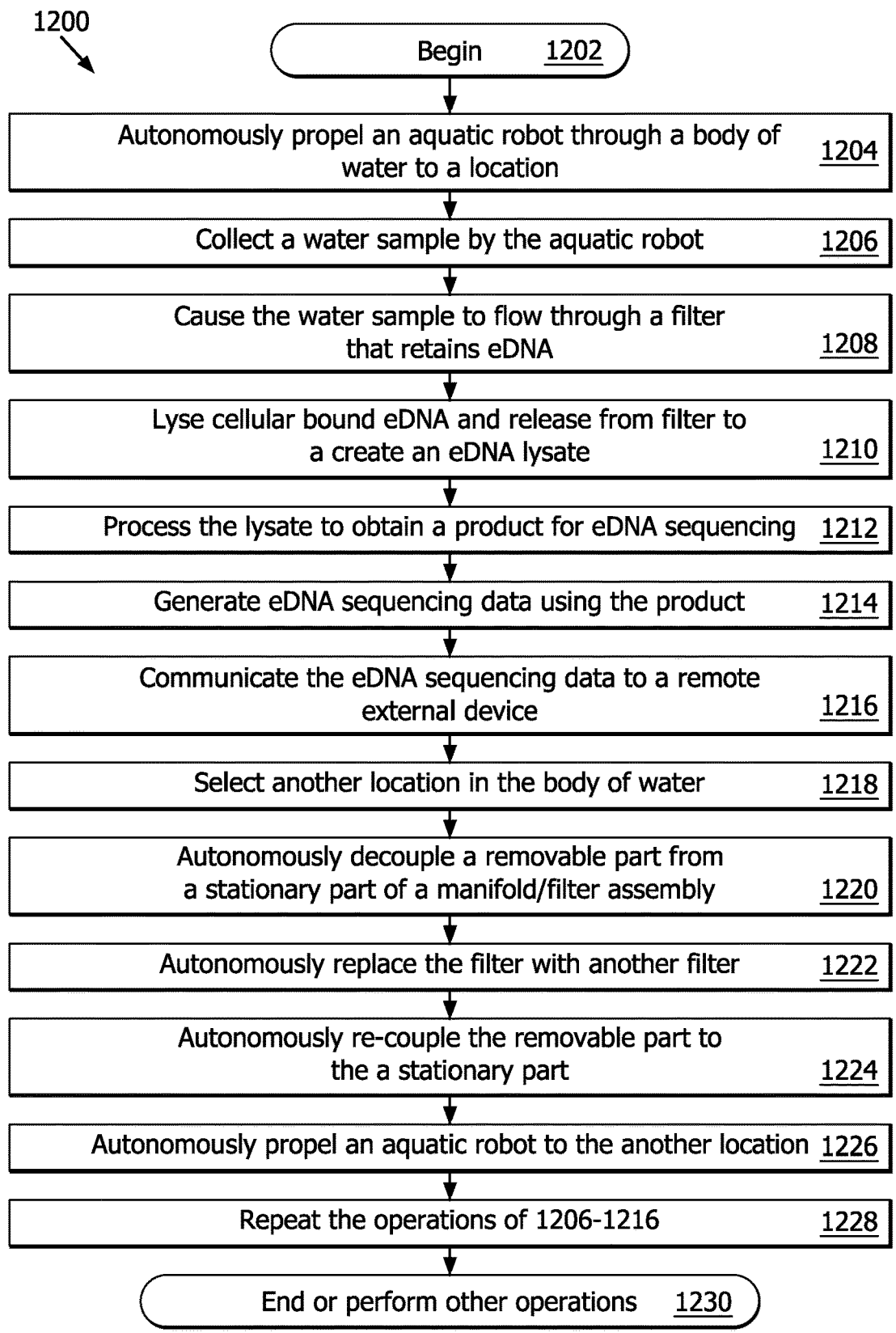
FIGS. 12A-12B ("collectively referred to herein as "FIG. 12") provide a flow diagram of an illustrative method for operating an aquatic robot.
Figure 12B:
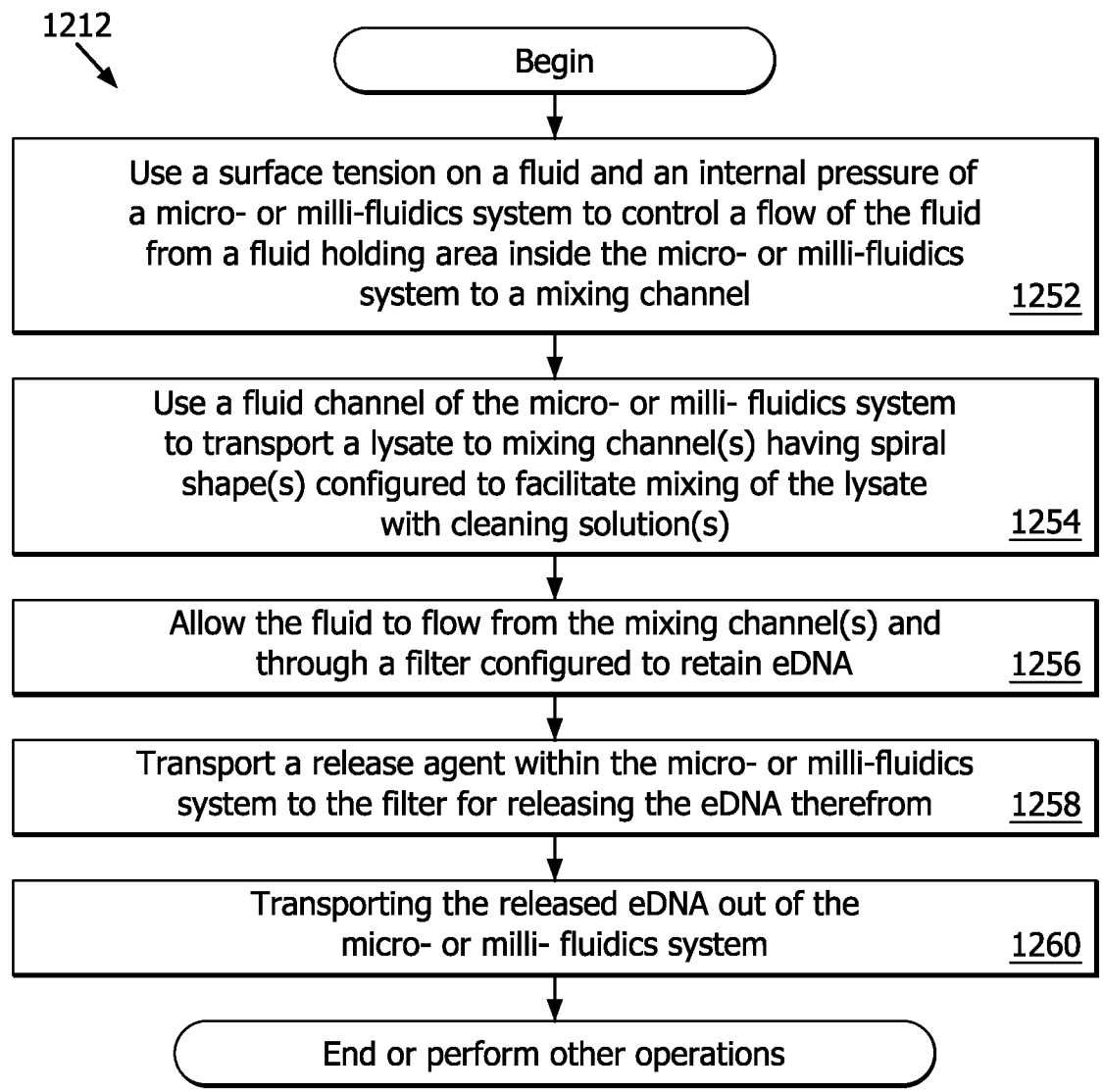

Next as shown by block 1214 of FIG. 12A, the aquatic robot generates eDNA sequencing data using the product output from the micro- or milli-fluidics system. The eDNA sequencing data is communicated in block 1216 from the aquatic robot to a remote external device (e.g., external device(s) 360 of FIG. 3).

The aquatic robot may select another location in the body of water, as shown by block 1218. This selection can be randomly made, made from a plurality of user-defined locations, or made based on machine learned information. Next in blocks 1220-1228, the aquatic robot can perform operations to autonomously: decouple a removable part from the stationary part of the single assembly; replace the filter with another filter; re-couple the removable part to the stationary part; propel itself through the body of water to the selected location; and repeat the operations of blocks 1206-1216. Subsequently, method 1200 ends or other operations are performed (e.g., return to 1202) as shown by block 1230.

Figure 13:
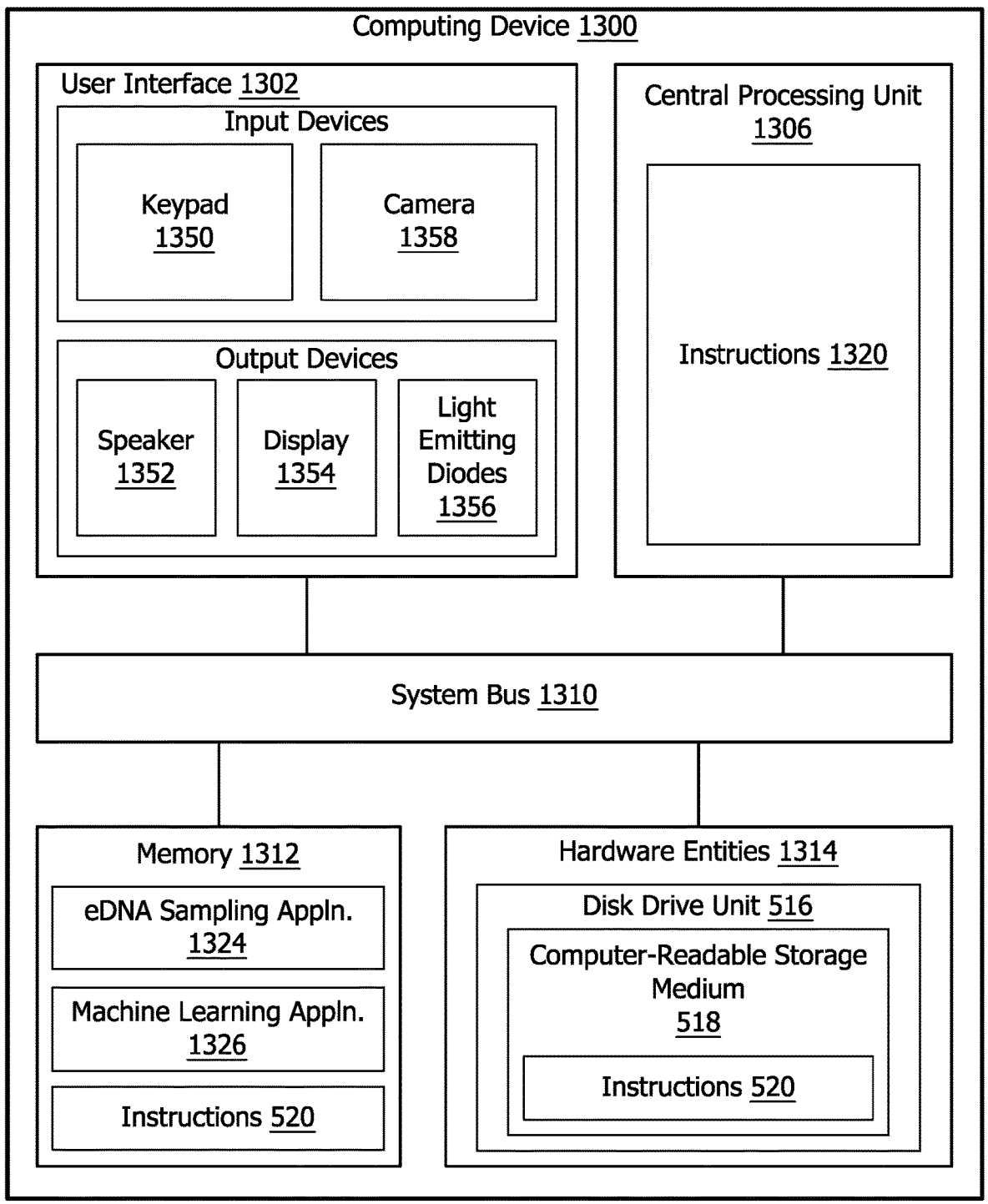
FIG. 13 provides a block diagram of a computing device.

Referring now to FIG. 13, there is provided a detailed block diagram of an illustrative architecture for a computing device 1300. Control system 450 and/or communication device 464 of FIG. 4 is/are the same as or substantially similar to computing device 1300. As such, the following discussion of computing device 1300 is sufficient for understanding components 450, 464 of FIG. 4.

Computing device 1300 may include more or less components than those shown in FIG. 13. However, the components shown are sufficient to disclose an illustrative embodiment implementing the present solution. The hardware architecture of FIG. 13 represents one embodiment of a representative computing device configured to facilitate autonomous operation of an eDNA-bot. As such, the computing device 1300 of FIG. 13 implements at least a portion of a method for operating an eDNA-bot in accordance with the present solution.

Some or all the components of the computing device 1300 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 13, the computing device 1300 comprises a user interface 1302, a central processing unit ("CPU") 1306, a system bus 1310, a memory 1312 connected to and accessible by other portions of computing device 1300 through system bus 1310, and hardware entities 1314 connected to system bus 1310. The user interface can include input devices (e.g., a keypad 1350 and/or a camera 1358) and output devices (e.g., a speaker 1352, a display 1354, and/or light emitting diodes ("LEDs") 1356), which facilitate user-software interactions for controlling operations of the computing device 1300.

At least some of the hardware entities 1314 perform actions involving access to and use of memory 1312, which can be a RAM, a disk driver and/or a Compact Disc Read Only Memory ("CD-ROM"). Hardware entities 1314 can include a disk drive unit 1316 comprising a computer-readable storage medium 1318 on which is stored one or more sets of instructions 1320 (e.g., software code) configured to implement one or more of the methodologies, procedures, or functions described herein. The instructions 1320 can also reside, completely or at least partially, within the memory 1312 and/or within the CPU 1306 during execution thereof by the computing device 1300. The memory 1312 and the CPU 1306 also can constitute machine-readable media. The term "machine-readable media", as used here, refers to a single medium or multiple media (e.g., a centralized or distributed database, and/or associated caches and servers) that store the one or more sets of instructions 1320. The term "machine-readable media", as used here, also refers to any medium that is capable of storing, encoding or carrying a set of instructions 1322 for execution by the computing device 1300 and that cause the computing device 1300 to perform any one or more of the methodologies of the present disclosure.

In some scenarios, the hardware entities 1314 include an electronic circuit (e.g., a processor) programmed for facilitating operations of an eDNA-bot. In this regard, it should be understood that the electronic circuit can access and run an eDNA sampling application 1324 and/or a machine learning application 1326 installed on the computing device 1300.

The machine learning application 1326 implements AI that provides the computing device 1300 with the ability to automatically learn and improve eDNA-bot operations from experience without being explicitly programmed. The machine learning application employs one or more machine learning algorithms that learn various information from accessed data (e.g., via pattern recognition and prediction making). Machine learning algorithms are well known in the art, and therefore will not be described herein in detail. Any known or to be known machine learning algorithm can be used herein without limitation. For example, in some scenarios, the machine learning application 1326 employs a supervised learning algorithm, an unsupervised learning algorithm, and/or a semi-supervised algorithm.

In summary, quantifying biodiversity (e.g., distributions, abundances, community composition) with conventional survey methods is costly, time-consuming, hazardous, and biased, creating uncertainties about what kind and how many of a particular species are in an area, which can greatly impact conservation, management, and mitigation plans. However, many of these biases can be overcome by using eDNA, and further improved upon by automating the eDNA pipeline for real-time data production. The eDNA-bot of the present solution provides fully functional remote, autonomous eDNA sampler, processor, sequencer, and analyzer providing eDNA results in real-time. Through the combination of micro- or milli-fluidics, ambient stable reagents, next-generation sequencing, and telemetry, eDNA-bot provides accurate real-time estimates of biodiversity, and concurrently reduce costs, contamination, and hazardous risks that often limit the scale and scope of biodiversity assessments. Long-term deployment of eDNA-bot and eDNA-bot's ability to analyze multiple samples without intervention allows for the collection time-series data which, despite the importance of temporal variation in species estimates, is data depauperate due to cost, and time constraints. Further, eDNA-bot is adaptable to specific user needs enabling a wide-range of questions to be answered through programmable and targeted data collection. For example, contaminants and pathogens found in wastewater treatment facilities can be quantified in real-time and reduce exposure of personnel to potential harm. With next-generation sequencing capabilities, eDNA-bot can provide real-time monitoring of new pathogenic variants and guide human health policies focused on emerging disease (e.g., COVID-19). eDNA-bot not only elevates and transforms the way in which vulnerable species are protected and invasive fronts are mitigated, but also facilitates tracking and heading off zoonotic pathogens and environmental contaminants that have wildlife, human health, biosecurity consequences.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, other than those illustrated and described may be employed in accordance with the spirit of the invention, and such changes, alternations and modifications as would occur to those skilled in the art are considered to be within the scope of this invention as broadly defined in the appended claims. In addition, it is to be understood that the phraseology and terminology employed herein are for the purpose of description and should not be regarded as limiting.

Without excluding further possible embodiments, certain example embodiments are summarized in the following clauses:

Clause 1. A method for operating an aquatic robot, comprising: autonomously propelling the aquatic robot through a body of water to a location where a water sample is to be obtained; and performing operations by the aquatic robot to autonomously: collect the water sample, cause the water sample to flow through a filter that retains eDNA, lyses and releases the eDNA to a create a lysate, process the lysate to obtain a product for eDNA sequencing, generate eDNA sequencing data using the product, and communicate the eDNA sequencing data to a remote external device.

Clause 2. The method according to clause 1, further comprising: autonomously propelling the aquatic robot through the body of water to another different location where another water sample is to be obtained; and repeating the operations by the aquatic robot using the another water sample.

Clause 3: The method according to any of the preceding clauses, further comprising selecting, by the aquatic robot, the another different location within the body of water randomly, from a plurality of user-defined locations, or based on machine learned information.

Clause 4: The method according to any of the preceding clauses, wherein the filter is integrated with a manifold into a single assembly comprising: a stationary part; a removable part removably coupled to the stationary part; an inlet channel extending around a circumference of the removable part and configured to cause a fluid to flow from an inlet port towards the filter that is disposed inside the removable part; and an outlet channel spaced apart from the inlet channel, extending around the circumference of the removable part, and configured to cause a filtered fluid to flow from the filter to an outlet port of the single assembly.

Clause 5. The method according to any of the preceding clauses, further comprising autonomously decoupling the removable part from the stationary part, replacing the filter with another filter, and re-coupling the removable part to the stationary part.

Clause 6. The method according to any of the preceding clauses, wherein the lysate is processed using a micro- or milli-fluidics system comprising a 3D printed part.

Clause 7. The method according to any of the preceding clauses, wherein the operations to process the lysate comprise using a fluid channel of the micro- or milli-fluidics system to transport the lysate to at least one mixing channel having a spiral shape configured to facilitate mixing of the lysate with a cleaning solution.

Clause 8. The method according to any of the preceding clauses, wherein the operations to process the lysate further comprise using a surface tension on the fluid and an internal pressure of the micro- or milli-fluidics system to control a flow of the fluid from a fluid holding area inside the micro- or milli-fluidics system to the at least one mixing channel.

Clause 9. The method according to any of the preceding clauses, wherein the operations to process the lysate further comprise allowing the fluid to flow from the at least one mixing channel and through another filter configured to retain DNA.

Clause 10. The method according to any of the preceding clauses, wherein the operations to process the lysate further comprise: transporting a release agent within the micro- or milli-fluidics system to the another filter for releasing the eDNA therefrom; and transporting the released eDNA out of the micro- or milli-fluidics system.

Clause 11. A system comprising means for performing the steps of any of the above method claims.

Clause 12. A system, comprising: a propulsion system; and an aquatic robot configured to (i) autonomously control the propulsion system to be propelled through a body of water and (ii) perform sequencing operations to autonomously collect a water sample at a location in the body of water to which the aquatic robot was propelled, cause the water sample to flow through a filter that retains eDNA, use the eDNA to a create a lysate, process the lysate to obtain a product for eDNA sequencing, generate eDNA sequencing data using the product, and communicate the eDNA sequencing data to a remote external device.

Clause 13. The system according to clause 12, wherein the aquatic robot is further configured to: control the propulsion system to be autonomously propelled through the body of water to another different location where another water sample is to be obtained; and repeat the sequencing operations using the another water sample.

Clause 14. The system according to any of the preceding clauses, wherein the aquatic robot is further configured to select the another different location within the body of water randomly, from a plurality of user-defined locations, or based on machine learned information.

Clause 15. The system according to any of the preceding clauses, wherein the filter is integrated with a manifold into a single assembly comprising: a stationary part; a removable part removably coupled to the stationary part; an inlet channel extending around a circumference of the removable part and configured to cause a fluid to flow from an inlet port towards the filter that is disposed inside the removable part; and an outlet channel spaced apart from the inlet channel, extending around the circumference of the removable part, and configured to cause a filtered fluid to flow from the filter to an outlet port of the single assembly.

Clause 16. The system according to any of the preceding clauses, wherein the aquatic robot is further configured to autonomously decouple the removable part from the stationary part, replace the filter with another filter, and re-couple the removable part to the stationary part.

Clause 17. The system according to any of the preceding clauses, wherein the aquatic robot comprises a micro- or milli-fluidics system comprising a 3D printed part that is configured to perform eDNA purification.

Clause 18. The system according to any of the preceding clauses, wherein the 3D printed part comprises at least one fluid channel configured to transport the lysate to at least one mixing channel having a spiral shape configured to facilitate mixing of the lysate with a cleaning solution.

Clause 19. The system according to any of the preceding clauses, wherein the 3D printed part further comprises a fluid holding area size and shaped to control a flow of the fluid to the at least one mixing channel based on a surface tension on the fluid and an internal pressure of the micro- or milli-fluidics system.

Clause 20. The system according to any of the preceding clauses, wherein the 3D printed part is further configured to allow the fluid to flow from the at least one mixing channel and through another filter configured to retain DNA.

Clause 21. The system according to any of the preceding clauses, wherein the 3D printed part is further configured to: transport a release agent within the micro- or milli-fluidics system to the another filter for releasing the eDNA therefrom; and transport the released eDNA out of the micro- or milli-fluidics system.

We claim:

1. A method for operating an aquatic robot, comprising:
   autonomously propelling the aquatic robot through a body of water to a location where a water sample is to be obtained; and
   performing operations by the aquatic robot to autonomously:
     collect the water sample;
     cause the water sample to flow through a filter that retains eDNA;
     lyse and release the eDNA to a create a lysate;
     process the lysate to obtain a product for eDNA sequencing;
     generate eDNA sequencing data using the product; and
     communicate the eDNA sequencing data to a remote external device;
   wherein the lysate is processed using a micro- or milli-fluidics system comprising a 3D printed part; and
   wherein the operations to process the lysate comprise using a fluid channel of the micro- or milli-fluidics system to transport the lysate to at least one mixing channel having a spiral shape configured to facilitate mixing of the lysate with a cleaning solution.

2. The method according to claim 1, further comprising:
   autonomously propelling the aquatic robot through the body of water to another different location where another water sample is to be obtained; and
   repeating the operations by the aquatic robot using the another water sample.

3. The method according to claim 2, further comprising selecting, by the aquatic robot, the another different location within the body of water randomly, from a plurality of user-defined locations, or based on machine learned information.

4. The method according to claim 1, wherein the operations to process the lysate further comprise using a surface tension on a fluid comprising the lysate mixed with the cleaning solution and an internal pressure of the micro- or milli-fluidics system to control a flow of the fluid from a fluid holding area inside the micro- or milli-fluidics system to the at least one mixing channel.

5. The method according to claim 1, wherein the operations to process the lysate further comprise allowing a fluid to flow from the at least one mixing channel and through another filter configured to retain DNA, the fluid comprising the lysate mixed with the cleaning solution.

6. The method according to claim 5, wherein the operations to process the lysate further comprise: transporting a release agent within the micro- or milli-fluidics system to the another filter for releasing the eDNA therefrom; and transporting the released eDNA out of the micro- or milli-fluidics system.

7. A method for operating an aquatic robot, comprising:
   autonomously propelling the aquatic robot through a body of water to a location where a water sample is to be obtained; and
   performing operations by the aquatic robot to autonomously:
     collect the water sample;
     cause the water sample to flow through a filter that retains eDNA;
     lyse and release the eDNA to a create a lysate;
     process the lysate to obtain a product for eDNA sequencing;
     generate eDNA sequencing data using the product; and
     communicate the eDNA sequencing data to a remote external device
   wherein the filter is integrated with a manifold into a single assembly comprising:
     a stationary part;
     a removable part removably coupled to the stationary part;
     an inlet channel extending around a circumference of the removable part and configured to cause a fluid to flow from an inlet port towards the filter that is disposed inside the removable part; and
     an outlet channel spaced apart from the inlet channel, extending around the circumference of the removable part, and configured to cause a filtered fluid to flow from the filter to an outlet port of the single assembly.

8. The method according to claim 7, further comprising autonomously decoupling the removable part from the stationary part, replacing the filter with another filter, and re-coupling the removable part to the stationary part.

9. A system, comprising:
   a propulsion system; and
   an aquatic robot configured to (i) autonomously control the propulsion system to be propelled through a body of water and (ii) perform sequencing operations to autonomously collect a water sample at a location in the body of water to which the aquatic robot was propelled, cause the water sample to flow through a filter that retains eDNA, use the eDNA to a create a lysate, process the lysate to obtain a product for eDNA sequencing, generate eDNA sequencing data using the product, and communicate the eDNA sequencing data to a remote external device;

wherein the aquatic robot comprises a micro- or milli-fluidics system comprising a 3D printed part that is configured to perform eDNA purification;
wherein the 3D printed part comprises at least one fluid channel configured to transport the lysate to at least one mixing channel having a spiral shape configured to facilitate mixing of the lysate with a cleaning solution.

10. The system according to claim 9, wherein the aquatic robot is further configured to:
control the propulsion system to be autonomously propelled through the body of water to another different location where another water sample is to be obtained; and
repeat the sequencing operations using the another water sample.

11. The system according to claim 10, wherein the aquatic robot is further configured to select the another different location within the body of water randomly, from a plurality of user-defined locations, or based on machine learned information.

12. The system according to claim 9, wherein the 3D printed part further comprises a fluid holding area sized and shaped to control a flow of a fluid to the at least one mixing channel based on a surface tension on the fluid and an internal pressure of the micro- or milli-fluidics system, the fluid comprising the lysate mixed with the cleaning solution.

13. The system according to claim 9, wherein the 3D printed part is further configured to allow a fluid to flow from the at least one mixing channel and through another filter configured to retain DNA, the fluid comprising the lysate mixed with the cleaning solution.

14. The system according to claim 13, wherein the 3D printed part is further configured to: transport a release agent within the micro- or milli-fluidics system to the another filter for releasing the eDNA therefrom; and transport the released eDNA out of the micro- or milli-fluidics system.

15. A system, comprising:
a propulsion system; and
an aquatic robot configured to (i) autonomously control the propulsion system to be propelled through a body of water and (ii) perform sequencing operations to autonomously collect a water sample at a location in the body of water to which the aquatic robot was propelled, cause the water sample to flow through a filter that retains eDNA, use the eDNA to a create a lysate, process the lysate to obtain a product for eDNA sequencing, generate eDNA sequencing data using the product, and communicate the eDNA sequencing data to a remote external device;
wherein the filter is integrated with a manifold into a single assembly comprising:
a stationary part;
a removable part removably coupled to the stationary part;
an inlet channel extending around a circumference of the removable part and configured to cause a fluid to flow from an inlet port towards the filter that is disposed inside the removable part; and
an outlet channel spaced apart from the inlet channel, extending around the circumference of the removable part, and configured to cause a filtered fluid to flow from the filter to an outlet port of the single assembly.

16. The system according to claim 15, wherein the aquatic robot is further configured to autonomously decouple the removable part from the stationary part, replace the filter with another filter, and re-couple the removable part to the stationary part.

* * * * *